United States Patent
Chi et al.

(10) Patent No.: US 9,505,799 B2
(45) Date of Patent: Nov. 29, 2016

(54) 18F-LABELED PRECURSOR OF PET RADIOACTIVE MEDICAL SUPPLIES, AND PREPARATION METHOD THEREOF

(75) Inventors: Dae-Yoon Chi, Seoul (KR); Byoung-Se Lee, Incheon (KR); Chansoo Park, Seoul (KR); Min-Hyung Lee, Goyang-si (KR); Hyojin Cha, Bucheon-si (KR); Woojin Cho, Seoul (KR); Heewon Kang, Seongnam-si (KR); Kyunghun Kim, Seoul (KR)

(73) Assignee: Futurechem Co., Ltd., Seoul (KR)

( * ) Notice: Subject to any disclaimer, the term of this patent is extended or adjusted under 35 U.S.C. 154(b) by 179 days.

(21) Appl. No.: 14/117,271

(22) PCT Filed: May 11, 2012

(86) PCT No.: PCT/KR2012/003713
§ 371 (c)(1),
(2), (4) Date: Nov. 12, 2013

(87) PCT Pub. No.: WO2012/157900
PCT Pub. Date: Nov. 22, 2012

(65) Prior Publication Data
US 2014/0194620 A1    Jul. 10, 2014

(30) Foreign Application Priority Data
May 13, 2011 (KR) .................. 10-2011-0045390

(51) Int. Cl.
| | | |
|---|---|---|
| *C07D 249/04* | (2006.01) | |
| *C07D 249/06* | (2006.01) | |
| *C07J 43/00* | (2006.01) | |
| *A61K 51/04* | (2006.01) | |
| *C07D 233/60* | (2006.01) | |
| *C07B 59/00* | (2006.01) | |
| *C07C 43/225* | (2006.01) | |
| *C07C 229/36* | (2006.01) | |

(52) U.S. Cl.
CPC .............. *C07J 43/003* (2013.01); *A61K 51/04* (2013.01); *A61K 51/0406* (2013.01); *A61K 51/0493* (2013.01); *C07B 59/00* (2013.01); *C07B 59/007* (2013.01); *C07C 43/225* (2013.01); *C07C 229/36* (2013.01); *C07D 233/60* (2013.01); *C07D 249/04* (2013.01); *C07D 249/06* (2013.01)

(58) Field of Classification Search
None
See application file for complete search history.

(56) References Cited

U.S. PATENT DOCUMENTS

| | | | | |
|---|---|---|---|---|
| 2006/0018966 A1* | 1/2006 | Lin | ...................... | A61K 9/0019 424/484 |
| 2009/0171098 A1* | 7/2009 | Bara | .................... | C07D 207/20 548/335.1 |
| 2010/0111864 A1 | 5/2010 | Ametamey et al. | | |

FOREIGN PATENT DOCUMENTS

| | | |
|---|---|---|
| KR | 10-2004-0065076 | 7/2004 |
| WO | 2006/065038 A1 | 6/2006 |

OTHER PUBLICATIONS

CAS RN 458567-03-8, STN® Registry, Availability date Oct. 3, 2002, Accessed Jun. 3, 2015.*
International Search Report issued in International App. No. PCT/KR2012/003713, mailed Nov. 14, 2012.
Moon, Byung Suk et al.; "A novel Aromatic Fluorine-18 Labeling Method Using Lodonium Salts Precursor"; Nuclear Medicine and Molecular Imaging, 2009; vol. 43, No. 1, pp. 1-9; ISSN 1869-3482.

* cited by examiner

*Primary Examiner* — Alicia L Otton
(74) *Attorney, Agent, or Firm* — Greer, Burns & Crain, Ltd.

(57) ABSTRACT

The present invention relates to a precursor of positron emission tomography (PET) radioactive medical supplies, a preparation method thereof, and an application thereof, and more specifically, to a precursor having a tetravalent organic salt leaving group, a preparation method, and a method for preparing desired PET radioactive medical supplies in a high radiochemical yield within a short preparation time by introducing $^{18}F$ using the same through a single step. The precursor having a tetravalent organic salt leaving group of the present invention can simplify the known complex multistep preparation of radioactive medical supplies into a single step, can save production costs because an excessive amount of a phase transfer catalyst is not required, facilitates separation of a compound after reaction, and enables rapid reaction velocity. The features are appropriate for the mass production of PET radioactive medical supplies by an automated synthesis system.

5 Claims, 1 Drawing Sheet

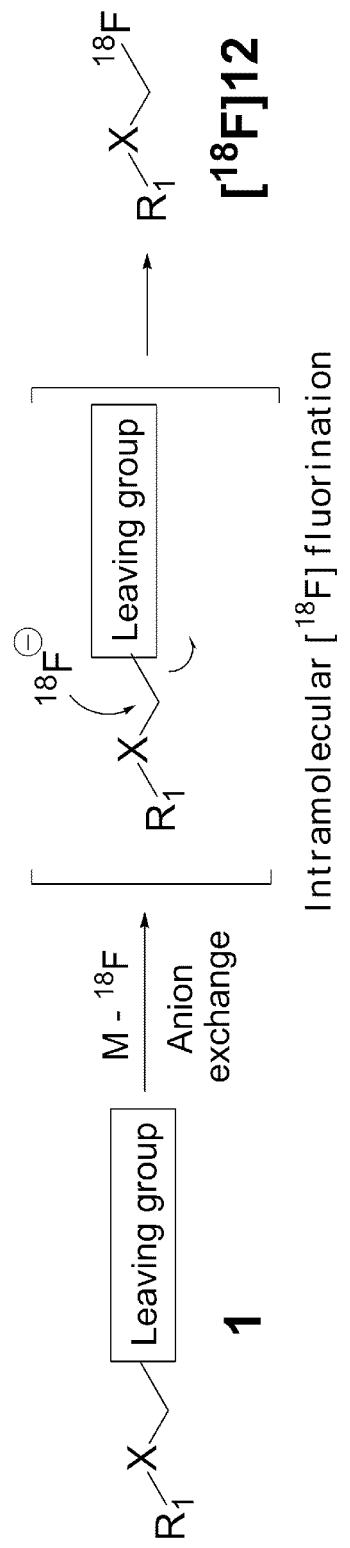

18F-LABELED PRECURSOR OF PET RADIOACTIVE MEDICAL SUPPLIES, AND PREPARATION METHOD THEREOF

This application is a U.S. National Phase under 35 U.S.C §371 of International Application No. PCT/KR2012/003713 filed on May 11, 2012, claiming the priority based on Korean Patent Application No. 10-2011-0045390 filed on May 13, 2011, the contents of all of which are incorporated herein by reference in their entirety.

TECHNICAL FIELD

The present disclosure relates to a precursor of radiopharmaceutical for positron emission tomography (PET), and a preparation method and the application thereof, in particular, provides a precursor having a leaving group of a tetravalent organic salt, a preparation method thereof, and a method for preparing a high radiochemical yield rate of a desired $^{18}$F-labeled PET radiopharmaceutical within a short preparation time by introducing $^{18}$F through a single step, while using the precursor.

BACKGROUND ART

Positron emission tomography (PET) is a nuclear medicine molecular imaging technique, which images the human body in real time, and shows rapid growth in the medical imaging market as an effective human body imaging technique, which can detect biochemical and physiological changes occurring in the human body at the beginning of a disease. The early researches of PET pharmaceuticals for a new disease use $^{11}$C, which is a positron emission radioactive isotope, since labeling is relatively easy, and $^{11}$C is a carbon, which is a framework of an organic substance. However, since $^{11}$C has the short half life of 20 minutes, it is not suitable for commercial use.

Meanwhile, $^{18}$F, which is another radioactive isotope, has various superior properties, for example, in that it can be easily produced in a large scale from a cyclotron. Especially, since $^{18}$F has the relatively long half life of 110 minutes, it has been recently spotlighted as a commercially applicable nuclide. Due to the utility of $^{18}$F, in order to substitute a conventionally developed $^{11}$C-labeled compound with an $^{18}$F-labeled compound or introduce $^{18}$F to a newly developed disease-target compound, there has been generally used a method for introducing a [$^{18}$F]fluoroprophyl functional group. However, a radiopharmaceutical, to which the [$^{18}$F]fluoroprophyl functional group is introduced, shows the tendency of decrease in the bonding force to a target material. Due to increase of lipophilicity, high intake occurs in some tissues. Due to increase of non-specific bonding, selectivity is reduced, and thereby, deteriorating an image. These problems can be resolved by introducing a [$^{18}$F]fluoromethyl group, which is similar in structure to a [$^{11}$C] methyl group, instead of the [$^{18}$F]fluoroprophyl functional group.

The conventional method for introducing a [$^{18}$F]fluoromethyl group uses a [$^{18}$F]fluoromethylated reagent. This reagent can be generally obtained by labeling $^{18}$F to a methane compound having at least two leaving groups. When the reagent is subjected to a nucleophilic substitution reaction with a precursor, a desired radiopharmaceutical, to which a [$^{18}$F]fluoromethyl group has been introduced, can be prepared. However, this method requires a two-step synthesis process for the $^{18}$F labeling, and thereby, causing complexity in process and lengthening the preparation time. The complicated preparation process makes it difficult to realize an automatic synthesis system necessary for commercialization.

DISCLOSURE OF THE INVENTION

Problems to be Solved by the Invention

A purpose of the present disclosure is to provide a precursor of a tetravalent organic salt to prepare an $^{18}$F-labeled PET radiopharmaceutical.

The other purpose of the present disclosure is to provide a preparation method for a precursor of a tetravalent organic salt to prepare an $^{18}$F-labeled PET radiopharmaceutical.

Another purpose of the present disclosure is to provide a nucleophilic fluorination reaction using a precursor of a tetravalent organic salt.

Another purpose of the present disclosure is to provide an $^{18}$F-labeled PET radiopharmaceutical prepared through a nucleophilic fluorination reaction of a precursor of a tetravalent organic salt.

Means for Solving the Problems

In order to achieve the objective, the present disclosure provides a precursor including a leaving group of a tetravalent organic salt, represented by the following Chemical Formula 1:

[Chemical Formula 1]

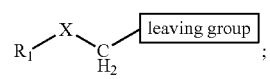

wherein, in Chemical Formula 1, $R_1$ is a part excluding a —X—$CH_2$—$^{18}$F part from an $^{18}$F-labeled radiotracer and represents a $C_1$-$C_{1000}$ hydrocarbon group in which a carbon in the main chain of the $C_1$-$C_{1000}$ hydrocarbon group may be non-replaced or replaced by an oxygen, a nitrogen, a sulfur, a phosphorus or combinations thereof and a hydrogen in the main chain may be non-replaced or replaced by a halogen, X represents an oxygen, a sulfur or —C(O)—, and the leaving group represents a non-substituted or a substituted $C_2$-$C_{50}$ tetravalent ammonium salt.

Desirably, in Chemical Formula 1, $R_1$ represents a $C_1$-$C_{200}$ hydrocarbon group in which a carbon in the main chain of the $C_1$-$C_{200}$ hydrocarbon group may be non-replaced or replaced by an oxygen, a nitrogen, a sulfur, a phosphorus or combinations thereof and a hydrogen in the main chain may be non-replaced or replaced by a halogen; X represents an oxygen, a sulfur or —C(O)—; the leaving group represents

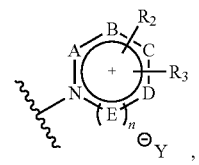

in which A, B, C, D and E independently represent a nitrogen, an oxygen, a sulfur or a carbon, respectively, (i) a hydrogen in each carbon may be non-replaced or replaced by $R_2$ or $R_3$, and (ii) each nitrogen may be non-substituted or substituted with $R_2$ or $R_3$, $R_2$ and $R_3$ are independently a $C_1$-$C_{20}$ hydrocarbon group in which a carbon in the main chain of the $C_1$-$C_{20}$ hydrocarbon may be non-replaced or replaced by an oxygen, a nitrogen, a sulfur or combinations thereof and a hydrogen in the main chain may be non-replaced or replaced by a halogen; Y is selected from the group consisting of a halogen anion, a sulfonate anion, $BF_4^-$, $PF_6^-$, $SbF_6^-$, $N(SO_2CF_3)_2^-$, and $N(CN)_2^-$, and n is 0 or 1.

Desirably, in Chemical Formula 1, $R_1$ represents a $C_1$-$C_{100}$ hydrocarbon group in which a carbon in the main chain of the $C_1$-$C_{100}$ hydrocarbon group may be non-replaced or replaced by an oxygen, a nitrogen, a sulfur, a phosphorus or combinations thereof and a hydrogen in the main chain may be non-replaced or replaced by a halogen; X represents an oxygen, a sulfur or —C(O)—; and the leaving group is a salt consisting of (i) a tetravalent cation and (ii) an anion of Y, the salt is selected from

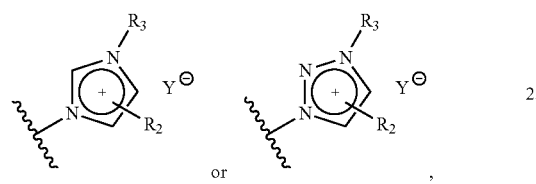

one nitrogen within the ring of the tetravalent cation is substituted with $R_3$, and each carbon within the ring of the tetravalent cation may be independently non-substituted or substituted with $R_2$, respectively, $R_2$ and $R_3$ are a $C_1$-$C_{20}$ hydrocarbon group in which a carbon in the main chain of the $C_1$-$C_{20}$ hydrocarbon group may be non-replaced or replaced by an oxygen, a nitrogen, a sulfur or combinations thereof and a hydrogen in the main chain may be non-replaced or replaced by a halogen; and Y is independently selected from the group consisting of trifluoromethanesulfonate ($CF_3SO_3^-$), paratolunesulfonate, methanesulfonate and paranitrobenzenesulfonate.

Desirably, in Chemical Formula 1, $R_1$ is selected from the group consisting of

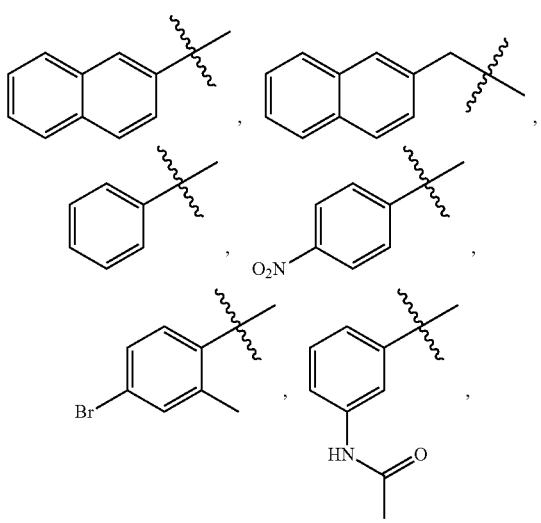

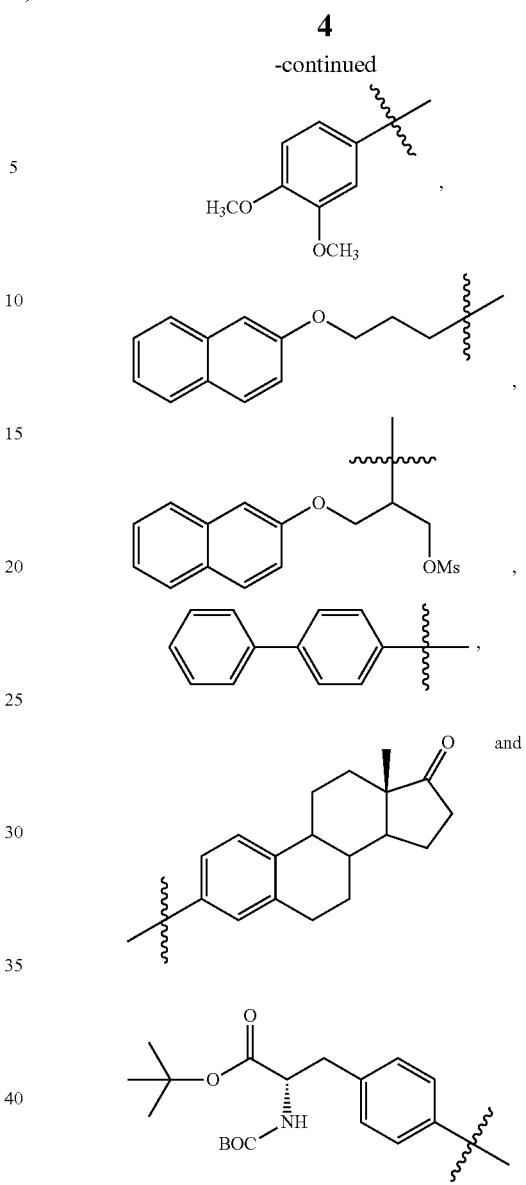

X represents an oxygen, a sulfur or —C(O)—, the leaving group is a salt consisting of (i) a tetravalent cation and (ii) an anion of Y, the salt is selected from

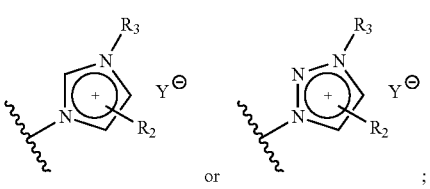

one nitrogen within the ring of the tetravalent cation is substituted with $R_3$, and each carbon in the ring of the tetravalent cation may be independently non-substituted or substituted with $R_2$, respectively, $R_2$ and $R_3$ are independently selected from the group consisting of a straight or branched chain of $C_{1-4}$ alkyl group for example, methyl, ethyl, n-propyl, iso-propyl, n-butyl, iso-butyl, t-butyl etc., phenyl,

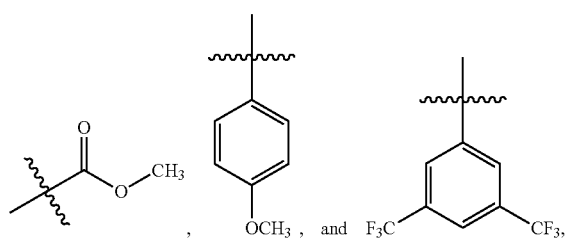

Y is independently selected from the group consisting of trifluoromethanesulfonate ($CF_3SO_3^-$), paratolunesulfonate, methanesulfonate and paranitrobenzenesulfonate.

Desirably, the precursor represented by Chemical Formula 1 is selected from the group consisting of 4-tert-butyl-3-methyl-1-[(2-naphthoxy)methyl]-1,2,3-triazolium trifluoromethanesulfonate; 4-methoxycarbonyl-3-methyl-1-[(2-naphthoxy)methyl]-1,2,3-triazolium trifluoromethanesulfonate; 4-[3,5-di(trifluoromethyl)phenyl]-3-methyl-1-[(2-naphthoxy)methyl]-1,2,3-triazolium trifluoromethanesulfonate; 4-(4-methoxyphenyl)-3-methyl-1-[(2-naphthoxy)methyl]-1,2,3-triazolium trifluoromethanesulfonate; 3-methyl-4-phenyl-1-(2-phenylethan-2-on-1-yl)-1,2,3-triazolium trifluoromethanesulfonate; 4-tert-butyl-3-methyl-1-[(phenylthio)methyl]-1,2,3-triazolium trifluoromethanesulfonate; 3-methyl-1-[(2-naphthoxy)methyl]-4-phenyl-1,2,3-triazolium trifluoromethanesulfonate; 3-methyl-1-[3-(2-naphthoxy)-n-propyl]oxymethyl-4-phenyl-1,2,3-triazolium trifluoromethanesulfonate; 1-[1-methylsulfonyloxy-3-(2-naphthyl)-2-oxypropyl]oxymethyl-3-methyl-4-phenyl-1,2,3-triazolium trifluoromethanesulfonate; 3-methyl-(2-naphthyl)methyl-oxymethyl-4-phenyl-1,2,3-triazolium trifluoromethanesulfonate; 3-methyl-1-[(2-naphthoxy)methyl]-4-phenylimidazolium trifluoromethanesulfonate; (s)-1-[4-[2-BOC-amino-2-(t-butoxycarbonyl)ethyl]phenyloxymethyl]-4-phenyl-1,2,3-triazolium trifluoromethanesulfonate; 1-(4-biphenyl)oxymethyl-3-methyl-4-phenyl-1,2,3-triazolium trifluoromethanesulfonate; 1-(4-bromo-2-methylphenyl)oxymethyl-3-methyl-4-phenyl-1,2,3-triazolium trifluoromethanesulfonate; 1-(3,4-dimethoxyphenyl)oxymethyl-3-methyl-4-phenyl-1,2,3-triazolium trifluoromethanesulfonate; 3-methyl-1-(4-nitrophenyl)oxymethyl-4-phenyl-1,2,3-triazolium trifluoromethanesulfonate; 1-(4-acetylaminophenyl)oxymethyl-3-methyl-4-phenyl-1,2,3-triazolium trifluoromethanesulfonate; 1-(3-O-estronyl)methyl-3-methyl-4-phenyl-1,2,3-triazolium trifluoromethanesulfonate; and 3-acetonaphthyl-1-methyl-imidazolium.

In addition, the present disclosure may be provided a preparation method for a precursor including a leaving group of a tetravalent organic salt represented by Chemical Formula 1, and, according to the present disclosure may be provided by various preparation methods depending on the sub-concept of Chemical Formula 1, specifically, may be provided by the following Preparation Methods 1 to 4.

Preparation Method 1

The present disclosure provides a preparation method for a compound of the following Chemical Formula 1-a, including, as shown in the following Reaction Scheme 1:

synthesizing an azido compound of the following Chemical Formula 3 from a compound represented by the following Chemical Formula 2 (step 1);

synthesizing a compound of the following Chemical Formula 5 through a [3+2] cycloaddition reaction between the azido compound of Chemical Formula 3 obtained in step 1 with an alkyne compound represented by the following Chemical Formula 4 (step 2); and reacting the compound of Chemical Formula 5 obtained in step 2 with an alkylation reagent represented by the following Chemical Formula 6 to synthesize an organic salt of the following Chemical Formula 1-a (step 3):

[Reaction Scheme 1]

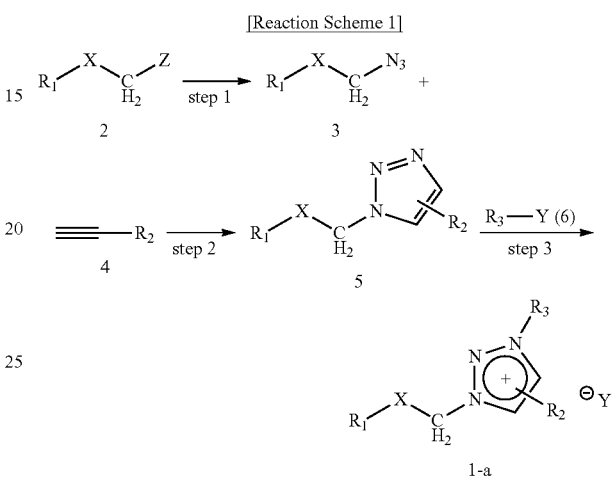

wherein, in Reaction Scheme 1, $R_1$, $R_2$, $R_3$ and Y are the same as defined above, and Z represents a chlorine, a bromine, a iodine or $R_4SO_3^-$, here, $R_4$ is a $C_1$-$C_{20}$ hydrocarbon group in which a carbon in the main chain of the $C_1$-$C_{20}$ hydrocarbon group may be non-replaced or replaced by an oxygen, a nitrogen, a sulfur or combinations thereof and hydrogen in the main chain may be non-replaced or replaced by a halogen.

In the preparation method for a precursor including a leaving group of a tetravalent organic salt according to the present disclosure, step 1 of Reaction Scheme 1 synthesizes an azido compound of Chemical Formula 3 from a compound represented by Chemical Formula 2. For the reagent and the reaction solvent used in step 1, a reagent and a reaction solvent generally used for an organic chemical reaction may be used. Step 2 of Reaction Scheme 1 synthesizes a compound of Chemical Formula 5 under a mild condition through cooper (I)-catalyzed alkyne/azide [3+2] cycloaddition (CuAAC) between the azido compound of Chemical Formula 3 obtained in step 1 with an alkyne compound represented by Chemical Formula 4. Here, the compounds of Chemical Formulas 2 and 3 are commercially available or can be synthesized by a convential method. For the reaction solvent used, a solvent generally used in the cooper (I)-catalyzed alkyne/azide [3+2] cycloaddition reaction between the azido compound with the alkyne compound may be used. Step 3 of Reaction Scheme 1 synthesizes an organic salt of Chemical Formula 1-a by reacting a 1,2,3-triazole compound of Chemical Formula 5 obtained in step 2 with an alkylated reagent represented by Chemical Formula 6. Here, the compound represented by Chemical Formula 6 is commercially available or can be synthesized by a general method. For the reaction solvent used, a solvent generally used in an organic salt preparation reaction may be used.

Preparation Method 2

The present disclosure provides a preparation method for a compound of the following Chemical Formula 1-b, including, as shown in the following Reaction Scheme 2:

synthesizing a compound of the following Chemical Formula 5 through a nucleophilic substitution reaction between a compound represented by the following Chemical Formula 7 with a compound represented by the following Chemical Formula 8 (step 1); and reacting the compound of the following Chemical Formula 5 obtained in step 1 with an alkylation reagent represented by the following Chemical Formula 6 to synthesize an organic salt of Chemical Formula 1-b (step 2):

[Reaction Scheme 2]

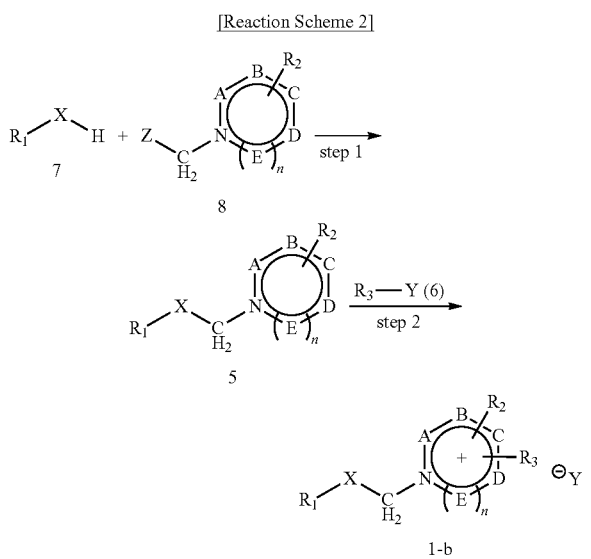

wherein, in Reaction Scheme 2, $R_1$, $R_2$, $R_3$, A, B, C, D, E, X, Y and n are the same as defined above, and Z is the same as defined in Preparation Method 1.

In the preparation method for a precursor compound of Chemical Formula 1 including a leaving group of a tetravalent organic salt according to the present disclosure, step 1 of Reaction Scheme 2 synthesizes a compound of Chemical Formula 5 through a nucleophilic substitution reaction between a compound represented by Chemical Formula 7 with a compound represented by Chemical Formula 8. Here, the compounds represented by Chemical Formulas 7 and 8 are commercially available or can be synthesized by a general method. For the reaction solvent used, a solvent generally used in the nucleophilic substitution reaction may be used. Step 2 of Reaction Scheme 2 synthesizes an organic salt of Chemical Formula 1-b by reacting the compound of Chemical Formula 5 obtained in step 1 with an alkylation reagent represented by Chemical Formula 6. Here, the compound represented by Chemical Formula 6 is commercially available or can be synthesized by a general method. For the reaction solvent used, a solvent generally used in a reaction for preparation of an organic salt may be used.

Preparation Method 3

The present disclosure provides a preparation method for preparing a compound of Chemical Formula 1-b, including, as shown in the following Reaction Scheme 3:

synthesizing a compound of Chemical Formula 1-b through a nucleophilic substitution reaction between a compound represented by Chemical Formula 7 with a compound represented by the following Chemical Formula 9 (step 1):

[Reaction Scheme 3]

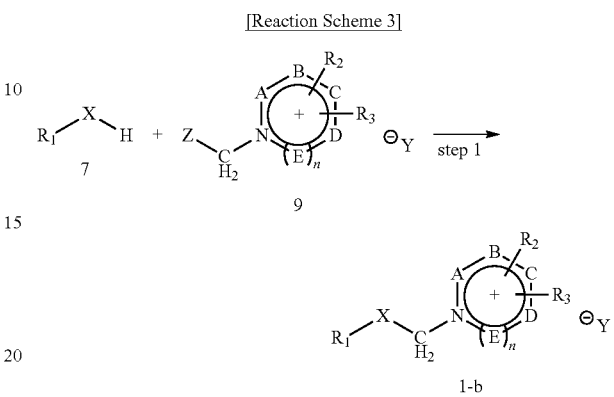

wherein, in Reaction Scheme 3, $R_1$, $R_2$, $R_3$, A, B, C, D, E, X, Y and n are the same as defined above, and Z is the same as defined in Preparation Method 1.

In the preparation method for a precursor compound of Chemical Formula 1 including a leaving group of a tetravalent organic salt according to the present disclosure, step 1 of Reaction Scheme 3 synthesizes a compound of Chemical Formula 1 through a nucleophilic substitution reaction between a compound represented by Chemical Formula 7 with a compound represented by Chemical Formula 9. Here, the compound represented by Chemical Formula 7 is commercially available or can be synthesized by a general method. The compound represented by Chemical Formula 9 can be synthesized by reacting the compound represented by Chemical Formula 8 in Preparation Method 2 with an alkylation reagent represented by Chemical Formula 6. For the reaction solvent used in step 1, a solvent generally used in a reaction for preparation of an organic salt may be used.

Preparation Method 4

The present disclosure provides a preparation method for a compound of Chemical Formula 1-b, including, as shown in the following Reaction Scheme 4:

synthesizing a compound of Chemical Formula 1-b through a nucleophilic substitution reaction between a compound represented by the following Chemical Formula 10 with a compound represented by the following Chemical Formula 11 (step 1):

[Reaction Scheme 4]

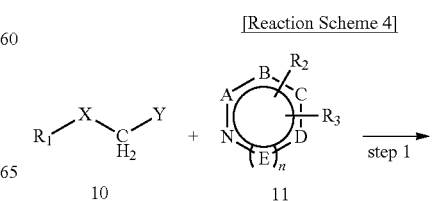

-continued

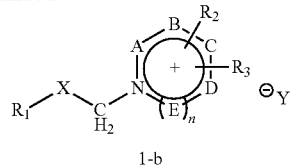

1-b wherein, in Reaction Scheme 4, $R_1$, $R_2$, $R_3$, A, B, C, D, E, X, Y and n are the same as defined above.

In the preparation method for a precursor compound of Chemical Formula 1 including a tetravalent organic salt leaving group according to the present disclosure, step 1 of Reaction Scheme 4 synthesizes an organic salt of Chemical Formula 1-b through a nucleophilic substitution reaction between a compound represented by Chemical Formula 10 with a compound represented by Chemical Formula 11. Here, the compounds represented by Chemical Formulas 10 and 11 are commercially available or can be synthesized by a general method. For the reaction solvent used, a solvent generally used in a reaction for preparation of an organic salt may be used.

In addition, the present disclosure provides a preparation method for an $^{18}$F-labeled compound, including, as shown in the following Reaction Scheme 5:

reacting a compound containing a leaving group of a tetravalent organic salt represented by Chemical Formula 1 with a fluorine salt represented by Chemical Formula M-F;

[Reaction Scheme 5]

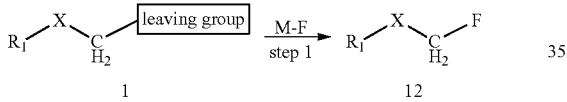

wherein, in Reaction Scheme 5, $R_1$, X and the leaving group are the same as defined above, M represents a metal cation selected from the group consisting of Li, Na, K, Rb and Cs; a tetravalent ammonium cation; or a tetravalent phosphonium cation, and F represents $^{18}$F.

The compound including a leaving group of a tetravalent organic salt of Chemical Formula 1 according to the present disclosure can be used as a precursor in a nucleophilic fluorination reaction with a fluoride anion in various metal salt or organic salt form as shown in FIG. 1. In FIG. 1, an intermediate compound is generated from anion exchange caused by interaction between a tetravalent organic salt precursor and a fluoride anion in the metal salt form or the organic salt form. The intermediate compound is rapidly converted into an F-labeled compound of Chemical Formula 12, which is a resulting product through a nucleophilic fluorination reaction within molecules. Here, the nucleophilic fluorination reaction (F is $^{18}$F) may be conducted under a generally used reaction condition.

Furthermore, the present disclosure provides an $^{18}$F-labeled compound, which is a resulting product of Reaction Scheme 5.

Effect of the Invention

The precursor of the present disclosure can introduce an $^{18}$F-fluoromethyl group to radiopharmaceutical through a simple one-step process. The present disclosure has an effect on simplifying conventional complicated multi-step synthesis by introducing an activated leaving group of a tetravalent organic salt to the precursor so as to prepare an $^{18}$F-fluoromethyl group through a one-step process. In addition, since the tetravalent organic salt included in the leaving group of the precursor serves as a phase transfer catalyst, an additional excessive amount of a phase transfer catalyst required for a common nuclerophilic [$^{18}$F]fluorination reaction is unnecessary. Accordingly, production costs can be reduced, and separation of a compound after a reaction is easy. The performance of the tetravalent organic salt in the precursor as a phase transfer catalyst induces a nucleophilic fluorination reaction within molecules, which is far faster in reaction velocity than a conventional nucleophilic fluorination reaction between molecules. These features are suitable for mass production of [$^{18}$F] radiopharmaceuticals by automated synthesis system.

BRIEF DESCRIPTION OF THE DRAWINGS

FIG. 1 shows a reaction scheme for preparing an $^{18}$F-labeled compound by using a precursor having a leaving group of a tetravalent organic salt of the present disclosure through a one-step process.

BEST MODE FOR CARRYING OUT THE INVENTION

Hereinafter, the present disclosure is described in more detail with reference to preparation examples and examples. However, the examples below merely illustrate the present disclosure, and the present disclosure is not limited thereto.

Preparation Example 1

Preparation of 2-(azidomethoxy)naphthalene (3a)

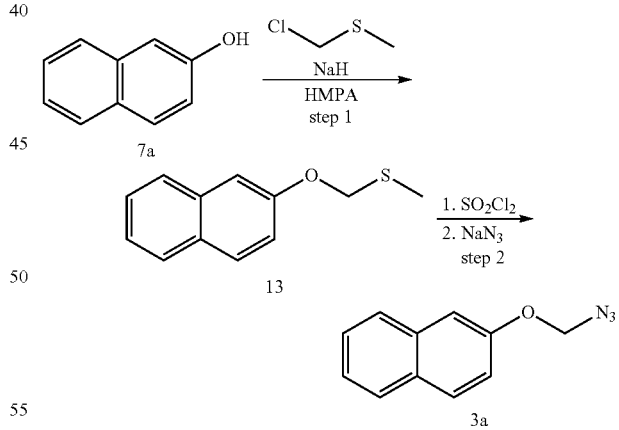

Step 1:

After 2-naphthol (7a, 1.15 g, 8.0 mmol) was dissolved in hexamethylphosphoramide (HMPA, 40 mL), sodium hydride (NaH, 352 mg, 8.8 mmol) was added thereto. The mixture was stirred for 30 minutes at a room temperature, and then, chloromethyl-methyl sulfide (0.737 mL, 8.8 mmol) was added thereto. Subsequently, the mixture was stirred for 16 hours at a room temperature. Once the reaction was terminated by adding water, an organic compound was extracted with ethyl acetate. The extracted ethyl acetate solution was treated with anhydrous sodium sulfate, and then, column chromatography (20% ethyl acetate/n-hexane) was performed to obtain a sulfide intermediate (13, 410 mg, 25%).

$^1$H NMR (500 MHz, CDCl$_3$) δ 2.26 (s, 3H), 5.22 (s, 2H), 7.20-7.16 (m, 2H), 7.34 (t, J=7.6 Hz, 1H), 7.43 (t, J=7.6 Hz, 1H), 7.73 (m, 3H)

Step 2:

After the sulfide compound (13, 410 mg, 2.0 mmol) obtained in step 1 was dissolved in dichloromethane, sulfurylchloride (1.0 M SO$_2$Cl$_2$/CH$_2$Cl$_2$ solution, 2.4 mL, 2.4 mmol) was slowly added thereto. The mixture was stirred for 30 minutes, and then, the solvent and the reaction residues were removed under vacuum. The remaining organic substance was dissolved again in a dimethylformamide (DMF) solvent, and then, sodium azide (NaN$_3$, 650 mg, 10 mmol) was added thereto. Subsequently, the mixture was stirred for 12 hours. Once the reaction was terminated by adding water, an organic compound was extracted with ethyl acetate. The extracted ethyl acetate solution was treated with anhydrous sodium sulfate, and then, column chromatography (10% ethyl acetate/n-hexane) was performed to obtain a desired compound, 2-(azidomethoxy)naphthalene (3a, 279 mg, 70%).

$^1$H NMR (500 MHz, CDCl$_3$) δ 5.27 (s, 2H), 7.21 (dd, J=9.0 Hz, J=2.5 Hz, 2H), 7.30 (d, J=2.5 Hz, 1H), 7.40-7.37 (m, 1H), 7.48-7.45 (m, 2H), 7.75 (d, J=8.0 Hz, 1H), 7.79 (d, J=9.0 Hz, 2H)

Preparation Example 2

Preparation of 2-azido acetophenone (3b)

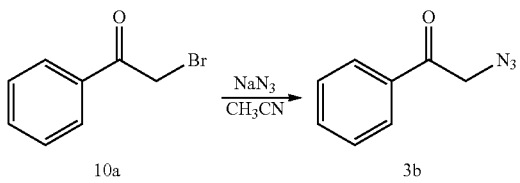

After 2-bromo acetophenone (10a, 1.97 g, 10.0 mmol) was dissolved in acetonitrile (40 mL), sodium azide (NaN$_3$, 650 mg, 11.0 mmol) was added thereto. Subsequently, the mixture was stirred for 12 hours. Once the reaction was terminated by adding water, an organic compound was extracted with dichloromethane. The extracted dichloromethane solution was treated with anhydrous sodium sulfate, and then, column chromatography (10% ethyl acetate/n-hexane) was performed to obtain a desired compound, 2-azido acetophenone (3b, 2.11 g, 100%).

$^1$H NMR (500 MHz, CDCl$_3$) δ 4.56 (s, 2H), 7.49 (t, J=6.2 Hz, 2H), 7.62 (t, J=6.0 Hz, 1H), 7.90 (d, J=7.6 Hz, 2H)

Preparation Example 3

Preparation of azidomethyl phenyl sulfide (3c)

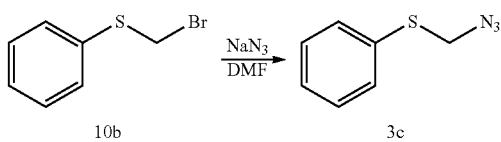

After bromomethyl phenyl sulfide (10b, 1.58 g, 10.0 mmol) was dissolved in dimethylformamide (40 mL), sodium azide (NaN$_3$, 1.3 g, 20.0 mmol) was added thereto. Subsequently, the mixture was stirred for 12 hours. Once the reaction was terminated by adding water, an organic compound was extracted with ethyl acetate. The extracted ethyl acetate solution was treated with anhydrous sodium sulfate, and then, column chromatography (1% ethyl acetate/n-hexane) was performed to obtain a desired compound, azidomethyl phenyl sulfide (3c, 1.62 g, 98%).

$^1$H NMR (500 MHz, CDCl$_3$) δ 4.54 (s, 2H), 7.37-7.25 (m, 3H), 7.45 (d, J=8.0 Hz, 2H)

Example 1

Preparation of 4-tert-butyl-3-methyl-1-[(2-naphthoxy)methyl]-1,2,3-triazolium trifluoromethanesulfonate (1a)

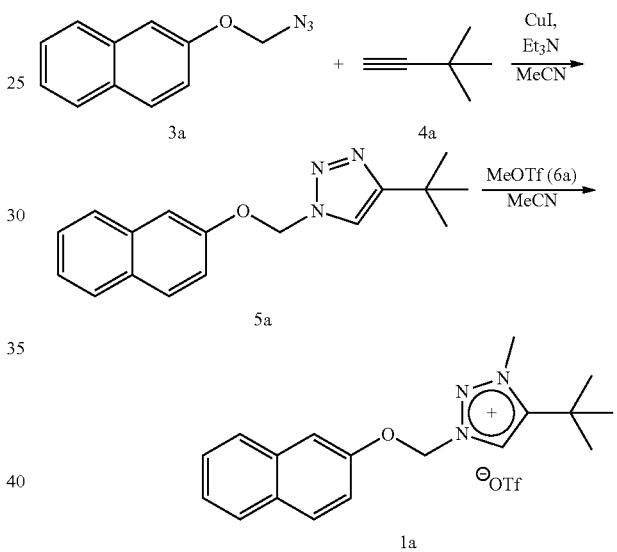

Step 1:

After the 2-(azidomethoxy)naphthalene (3a, 390 mg, 2.0 mmol) compound obtained in step 2 of Preparation Example 1 and 3,3-dimethyl-1-butyne (4a, 246 mg, 3.0 mmol) were dissolved in acetonitrile (8 mL), copper iodide (77 mg, 0.4 mmol) and triethylamine (0.056 mL, 0.4 mmol) were added thereto. The mixture was stirred for 2 hours at a room temperature, and then, reduced pressure to concentrate. Thereafter, column chromatography (1% methanol/dichloromethane) was performed was obtained a desired compound, 4-tert-butyl-1-[(2-naphthoxy)methyl]-1,2,3-triazole (5a, 477 mg, 85%).

$^1$H NMR (500 MHz, CDCl$_3$) δ 1.35 (s, 9H), 6.30 (s, 2H), 7.19 (dd, J=9.0 Hz, J=2.5 Hz, 1H), 7.40-7.38 (m, 1H), 7.46-7.44 (m, 2H), 7.51 (s, 1H), 7.76 (t, J=8.0 Hz, 3H);

$^{13}$C NMR (125 MHz, CDCl$_3$) δ 158.8, 154.3, 134.3, 130.14, 130.05, 127.8, 127.5, 126.9, 124.9, 118.7, 118.6, 109.9, 76.2, 31.0, 30.4

Step 2:

After 4-tert-butyl-1-[(2-naphthoxy)methyl]-1,2,3-triazole (5a, 477 mg, 1.69 mmol) obtained in step 1 was dissolved in acetonitrile (7.0 mL), methyl trifluoromethanesulfonate (6a, MeOTf, 0.278 mL, 2.5 mmol) was added thereto. The mixture was stirred for 30 minutes at 0° C., and then, the solvent was removed under a reduced pressure to obtained a desired compound, 4-tert-butyl-3-methyl-1-[(2-naphthoxy)methyl]-1,2,3-triazolium trifluoromethanesulfonate (1a, 580 mg, 77%).

$^1$H NMR (500 MHz, CDCl$_3$) δ 1.46 (s, 9H), 4.35 (s, 3H), 6.60 (s, 2H), 7.22 (dd, J=9.0, 2.5 Hz, 1H), 7.42-7.39 (m, 1H), 7.49-7.45 (m, 2H), 7.77 (d, J=8.0 Hz, 1H), 7.80 (t, J=8.5 Hz, 2H), 8.60 (s, 1H);

$^{13}$C NMR (125 MHz, CDCl$_3$) δ 153.1, 152.3, 134.1, 130.6, 130.4, 128.4, 127.8, 127.6, 127.2, 125.4, 120.8 (q, J=319 Hz), 118.0, 110.2, 79.2, 40.9, 31.6, 28.4.

Example 2

Preparation of 4-methoxycarbonyl-3-methyl-1-[(2-naphthoxy)methyl]-1,2,3-triazolium trifluoromethanesulfonate (1b)

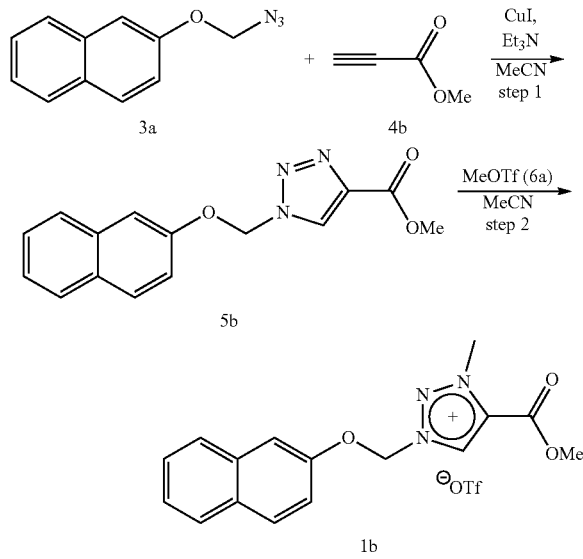

Step 1:

4-Methoxycarbonyl-1-[(2-naphthoxy)methyl]-1,2,3-triazole (5b, 346 mg, 61%) was obtained in the same manner as used in step 1 of Example 1, except that methylpropiolate (4b, 252 mg, 3.0 mmol) was used, instead of 3,3-dimethyl-1-butyne (4a) of step 1 of Example 1.

$^1$H NMR (500 MHz, CDCl$_3$) δ 3.94 (s, 3H), 6.41 (s, 2H), 7.17 (dd, J=9.0 Hz, J=2.5 Hz, 1H), 7.36 (d, J=2.5 Hz, 1H), 7.42-7.39 (m, 1H), 7.49-7.45 (m, 1H), 7.73 (d, J=8.0 Hz, 1H), 7.79-7.77 (m, 2H), 8.34 (s, 1H);

$^{13}$C NMR (125 MHz, CDCl$_3$) δ 161.0, 153.6, 141.0, 134.1, 130.5, 130.3, 127.9, 127.6, 127.4, 127.1, 125.2, 118.3, 110.2, 76.7, 52.5

Step 2:

4-methoxycarbonyl-3-methyl-1-[(2-naphthoxy)methyl]-1,2,3-triazolium trifluoromethanesulfonate (1b, 513 mg, 94%) was obtained in the same manner as used in step 2 of Example 1, except that 4-methoxycarbonyl-1-[(2-naphthoxy)methyl]-1,2,3-triazole (5b, 346 mg, 1.22 mmol) was used, instead of 4-tert-butyl-1-[(2-naphthoxy)methyl]-1,2,3-triazole (5a) of step 2 of Example 1.

$^1$H NMR (500 MHz, CDCl$_3$) δ 3.96 (s, 3H), 4.35 (s, 3H), 6.70 (s, 2H), 7.22 (dd, J=9.0 Hz, 2.5 Hz, 1H), 7.41 (td, J=7.8, 1.2 Hz, 1H), 7.47 (td, J=7.3, 1.3 Hz, 1H), 7.51 (d, J=2.5 Hz, 1H), 7.76 (d, J=8.0 Hz, 1H), 7.80 (t, J=9.0 Hz, 2H), 9.26 (s, 1H);

$^{13}$C NMR (125 MHz, CDCl$_3$) δ 155.4, 152.9, 134.1, 133.8, 133.3, 130.8, 130.7, 127.8, 127.7, 127.3, 125.6, 120.7 (t, J=318 Hz), 118.0, 110.9, 80.3, 54.3, 41.5

Example 3

Preparation of 4-[3,5-di(trifluoromethyl)phenyl]-3-methyl-1-[(2-naphthoxy)methyl]-1,2,3-triazolium trifluoromethanesulfonate (1c)

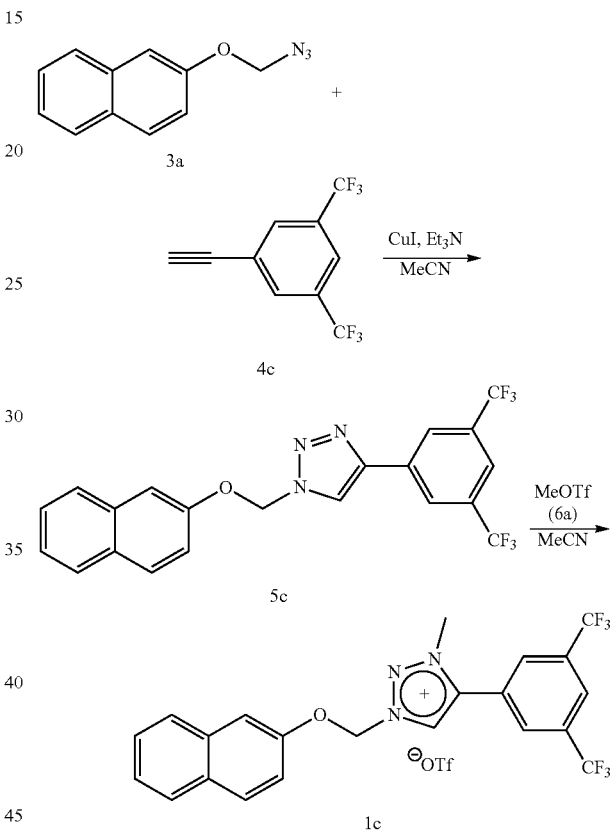

Step 1:

4-[3,5-Di(trifluoromethyl)phenyl]-1-((2-naphthoxy)methyl)-1,2,3-triazole (5c, 700 mg, 80%) was obtained in the same manner as used in step 1 of Example 1, except that 1-ethynyl-3,5-bis(trifluoromethyl)benzene (4c, 0.530 mL, 3.0 mmol) was used, instead of 3,3-dimethyl-1-butyne (4a) of step 1 of Example 1.

$^1$H NMR (500 MHz, CDCl$_3$) δ 6.45 (s, 2H), 7.20 (dd, J=9.0 Hz, J=2.5 Hz, 1H), 7.41-7.38 (m, 1H), 7.43 (d, J=2.5 Hz, 1H), 7.49-7.45 (m, 1H), 7.80-7.75 (m, 3H), 7.83 (s, 1H), 8.19 (s, 1H);

$^{13}$C NMR (125 MHz, CDCl$_3$) δ 134.2, 132.6, 132.4, 132.3, 130.4, 130.2, 127.9, 127.4, 127.1, 125.9, 125.2, 124.4, 122.2, 122.1, 120.7, 118.4, 109.9, 76.5

Step 2:

4-[3,5-Di(trifluoromethyl)phenyl]-3-methyl-1-[(2-naphthoxy)methyl]-1,2,3-triazolium trifluoromethanesulfonate (1c, 860 mg, 89%) was obtained in the same manner as used in step 2 of Example 1, except that 4-[3,5-di(trifluoromethyl)phenyl]-1-[(2-naphthoxy)methyl]-1,2,3-triazole (5c, 700 mg, 1.60 mmol) was used, instead of 4-tert-butyl-1-[(2-naphthoxy)methyl]-1,2,3-triazole (5a) of step 2 of Example 1.

$^1$H NMR (500 MHz, MeOD) δ 4.36 (s, 3H), 6.81 (s, 2H), 7.35 (dd J=9.0 Hz, 2.5 Hz, 1H), 7.43 (td, J=7.0 Hz, 1.0 Hz, 1H), 7.50 (td, J=7.0 Hz, 1.0 Hz, 1H), 7.64 (d, J=2.5 Hz, 1H), 7.85 (t, J=7.0 Hz, 2H), 7.73 (d, J=9.0 Hz, 1H), 8.33 (s, 1H), 8.36 (s, 2H);

$^{13}$C NMR (125 MHz, MeOD) δ 153.2, 141.2, 134.2, 132.7 (q, J=34 Hz), 130.6, 130.4 (d, J=3 Hz), 130.2, 127.4, 127.1, 126.7, 125.4 (q, J=4 Hz), 125.0, 124.9, 123.9, 121.8, 120.4 (q, J=317 Hz), 117.8, 110.7, 79.8, 38.4

Example 4

Preparation of 4-(4-methoxyphenyl)-3-methyl-1-[(2-naphthoxy)methyl]-1,2,3-triazolium trifluoromethanesulfonate (1d)

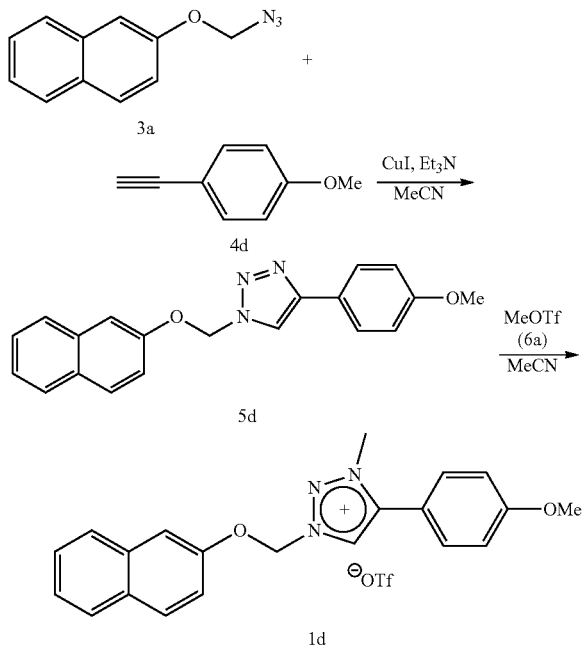

Step 1:

4-(4-Methoxyphenyl)-1-[(2-naphthoxy)methyl]-1,2,3-triazole (5d, 391 mg, 59%) was obtained in the same manner as used in step 1 of Example 1, except that 4-ethynyl anisole (4d, 252 mg, 3.0 mmol) was used, instead of 3,3-dimethyl-1-butyne (4a) of step 1 of Example 1.

$^1$H NMR (500 MHz, CDCl$_3$) δ 3.83 (s, 3H), 6.39 (s, 2H), 7.00-6.93 (m, 2H), 7.20 (dd, J=9.0 Hz, J=2.5 Hz, 1H), 7.27 (d, J=9.0 Hz, 1H), 7.40-7.37 (m, 1H), 7.47-7.44 (m, 2H), 7.78-7.72 (m, 5H), 7.93 (s, 1H);

$^{13}$C NMR (125 MHz, CDCl$_3$) δ 134.3, 133.9, 130.3, 130.2, 129.9, 127.8, 127.5, 127.4, 127.3, 127.0, 125.0, 123.0, 118.7, 118.6, 114.5, 110.1, 76.5, 55.5

Step 2:

4-(4-Methoxyphenyl)-3-methyl-1-[(2-naphthoxy)methyl]-1,2,3-triazolium trifluoromethanesulfonate (1d, 521 mg, 89%) was obtained in the same manner as used in step 2 of Example 1, except that 4-(4-methoxyphenyl)-1-[(2-naphthoxy)methyl]-1,2,3-triazole (5d, 391 mg, 1.18 mmol) was used, instead of 4-tert-butyl-1-[(2-naphthoxy)methyl]-1,2,3-triazole (5a) of step 2 of Example 1.

$^1$H NMR (500 MHz, CDCl$_3$) δ 3.82 (s, 3H), 4.25 (s, 3H), 6.65 (s, 2H), 7.03-7.00 (m, 2H), 7.25 (dd, J=9.0, 2.5 Hz, 1H), 7.42 (td, J=7.5, 1.0 Hz, 1H), 7.53-7.47 (m, 4H), 7.79 (d, J=8.5 Hz, 1H), 7.83 (t, J=9.0 Hz, 2H), 8.76 (s, 1H);

$^{13}$C NMR (125 MHz, CDCl$_3$) δ 162.7, 153.1, 144.1, 134.2, 131.3, 130.8, 130.6, 128.5, 127.8, 127.7, 118.0, 115.5, 113.5, 110.5, 79.6, 55.7, 38.9

Example 5

Preparation of 3-methyl-4-phenyl-1-(2-phenylethan-2-on-1-yl)-1,2,3-triazolium trifluoromethanesulfonate (1e)

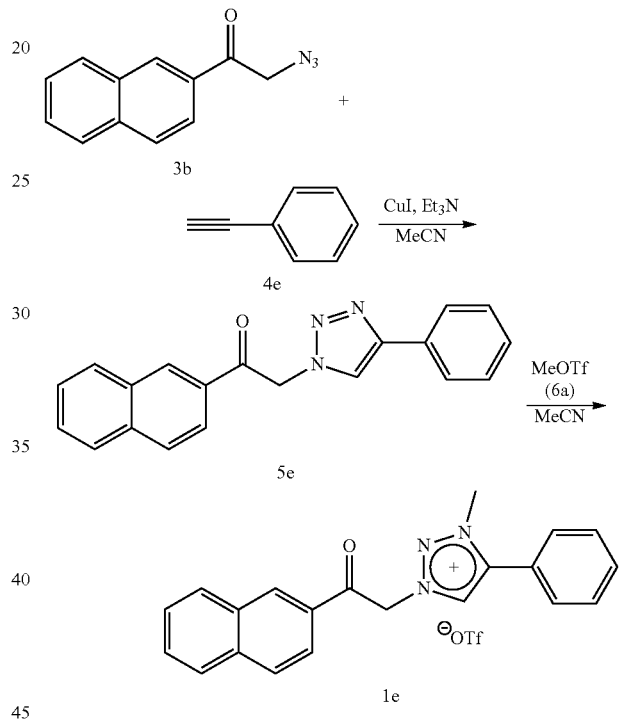

Step 1:

After 2-Azido acetophenone (3b, 322 mg, 2.0 mmol) and phenylacetylene (4e, 225 mg, 2.2 mmol) were dissolved in acetonitrile (8 mL), copper iodide (77 mg, 0.4 mmol) and triethylamine (0.056 mL, 0.4 mmol) were added thereto. The mixture was stirred for 2 hours at a room temperature, and then, concentrated under vacuum. Subsequently, column chromatography (1% methanol/dichloromethane) was performed to obtain a desired compound, 4-phenyl-1-(2-phenylethan-2-on-1-yl)-1,2,3-triazole (5e, 520 mg, 83%).

$^1$H NMR (500 MHz, CDCl$_3$) δ 5.90 (s, 2H), 7.35 (t, J=7.4 Hz, 1H), 7.44 (t, J=7.4 Hz, 2H), 7.55 (t, J=7.8 Hz, 2H), 7.68 (t, J=7.4 Hz, 1H), 7.87 (d, J=8.4 Hz, 2H), 7.95 (s, 1H), 8.03 (t, J=8.4 Hz, 2H)

Step 2:

After 4-phenyl-1-(2-phenylethan-2-on-1-yl)-1,2,3-triazole (5e, 520 mg, 1.67 mmol) obtained in step 1 was dissolved in acetonitrile (7.0 mL), methyl trifluoromethanesulfonate (6a, MeOTf, 0.278 mL, 2.5 mmol) was added thereto. The mixture was stirred for 30 minutes at 0° C., and then, the solvent was removed under a reduced pressure to obtain a desired compound, 3-methyl-4-phenyl-1-(2-phenylethan-2-on-1-yl)-1,2,3-triazolium trifluoromethanesulfonate (1e, 694 mg, 87%).

¹H NMR (500 MHz, CDCl₃) δ 4.31 (s, 3H), 6.43 (s, 2H), 7.55-7.72 (m, 8H), 8.04 (d, J=6.0 Hz, 2H), 8.76 (s, 1H)

Example 6

Preparation of 4-tert-butyl-3-methyl-1-[(phenylthio)methyl]-1,2,3-triazolium trifluoromethanesulfonate (1f)

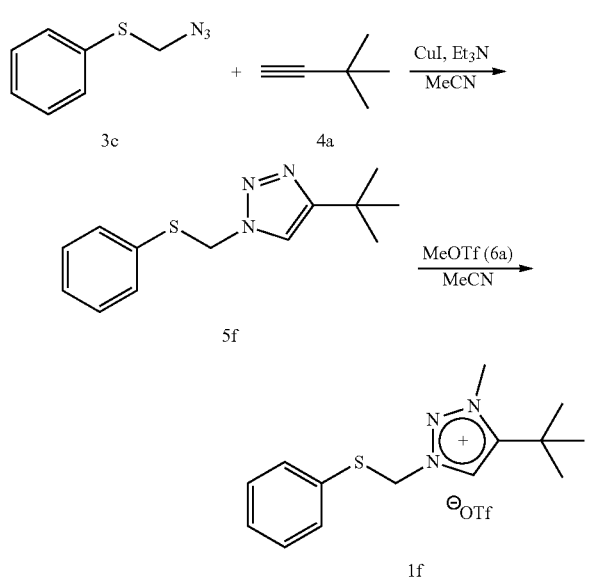

Step 1:

After azidomethyl phenyl sulfide (3c, 330 mg, 2.0 mmol) obtained in Preparation Example 3 and 3,3-dimethyl-1-butyne (4a, 246 mg, 3.0 mmol) were dissolved in acetonitrile (8 mL), copper iodide (77 mg, 0.4 mmol) and triethylamine (0.056 mL, 0.4 mmol) were added thereto. The mixture was stirred for 2 hours at a room temperature, and then, concentrated under a reduced pressure. Subsequently, column chromatography (1% methanol/dichloromethane) was performed to obtain a desired compound, 4-tert-butyl-1-[(phenylthio)methyl]-1,2,3-triazole (5f, 411 mg, 83%).

¹H NMR (500 MHz, CDCl₃) δ 1.23 (s, 9H), 5.90 (s, 2H), 7.45-7.34 (m, 5H), 7.76 (s, 1H).

Step 2:

After 4-tert-butyl-1-[(phenylthio)methyl]-1,2,3-triazole (5f, 411 mg, 1.66 mmol) obtained in step 1 was dissolved in acetonitrile (7.0 mL), methyl trifluoromethanesulfonate (6a, MeOTf, 0.278 mL, 2.5 mmol) was added thereto. The mixture was stirred for 30 minutes at 0° C., and then, the solvent was removed under a reduced pressure to obtain a desired compound, 4-tert-butyl-3-methyl-1-[(phenylthio)methyl]-1,2,3-triazolium trifluoromethanesulfonate (1f, 615 mg, 90%).

¹H NMR (500 MHz, CDCl₃) δ 1.46 (s, 9H), 4.28 (s, 3H), 5.93 (s, 2H), 7.43-7.38 (m, 5H), 8.17 (s, 1H).

Example 7

Preparation of 3-methyl-1-[(2-naphthoxy)methyl]-4-phenyl-1,2,3-triazolium trifluoromethanesulfonate (1g)

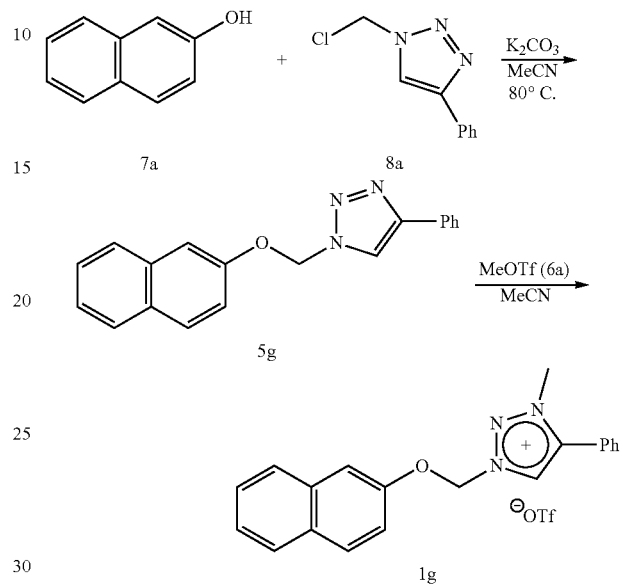

Step 1:

After 2-naphthol (7a, 720 mg, 5.0 mmol) and potassium carbonate (2.07 g, 15 mmol) were dissolved in acetonitrile (20 mL), 1-(chloromethyl)-4-phenyl-1,2,3-triazole (8a, 1.45 g, 7.5 mmol) was added thereto. The mixture was stirred for hours at the heating condition of 80° C. Once the reaction was terminated by adding water, an organic compound was extracted with ethyl acetate. The extracted ethyl acetate solution was treated with anhydrous sodium sulfate. Subsequently, column chromatography (30% ethyl acetate/n-hexane) was performed to obtain a desired compound, 4-phenyl-1-[(2-naphthoxy)methyl]-1,2,3-triazole (5g, 1.13 g, 75%).

¹H NMR (500 MHz, CDCl₃) δ 6.40 (s, 2H), 7.20 (dd, J=9.0 Hz, J=2.5 Hz, 1H), 7.26 (d, J=9.5 Hz, 1H), 7.47-7.31 (m, 6H), 7.79-7.76 (m, 3H), 7.83-7.81 (m, 2H), 8.01 (s, 1H);

¹³C NMR (125 MHz, CDCl₃) δ 134.2, 133.9, 130.3, 130.2, 129.9, 129.0, 128.6, 127.8, 127.5, 127.0, 126.03, 125.94, 125.0, 119.6, 118.5, 110.1, 76.5.

Step 2:

After 4-phenyl-1-[(2-naphthoxy)methyl]-1,2,3-triazole (5g, 1.13 g, 3.75 mmol) obtained in step 1 was dissolved in acetonitrile (15 mL), methyl trifluoromethanesulfonate (6a, MeOTf, 0.618 mL, 5.63 mmol) was added thereto. The mixture was stirred for 30 minutes at 0° C., and then, the solvent was removed under a reduced pressure to obtain a desired compound, 4-phenyl-3-methyl-1-[(2-naphthoxy)methyl]-1,2,3-triazolium trifluoromethanesulfonate (1g, 1.68 g, 96%).

¹H NMR (500 MHz, CDCl₃) δ 3.81 (s, 3H), 6.35 (s, 2H), 7.22 (dd, J=9.0 Hz, 2.0 Hz, 1H), 7.40-7.35 (m, 3H), 7.54-7.43 (m, 6H), 7.75 (d, J=8.0 Hz, 1H), 7.78 (d, J=9.0 Hz, 1H), 7.85 (t, J=8.5 Hz, 1H), 9.63 (s, 1H);

$^{13}$C NMR (125 MHz, CDCl$_3$) δ 152.8, 138.3, 136.6, 134.3, 131.1, 130.6, 130.4, 129.64, 129.60, 127.7, 127.2, 125.3, 124.5, 120.9 (d, J=319 Hz), 118.4, 118.1, 110.3, 76.0, 35.1.

Example 8

Preparation of 3-methyl-1-[3-(2-naphthoxy)-n-propyl]oxymethyl-4-phenyl-1,2,3-trizaolium trifluoromethanesulfonate (1h)

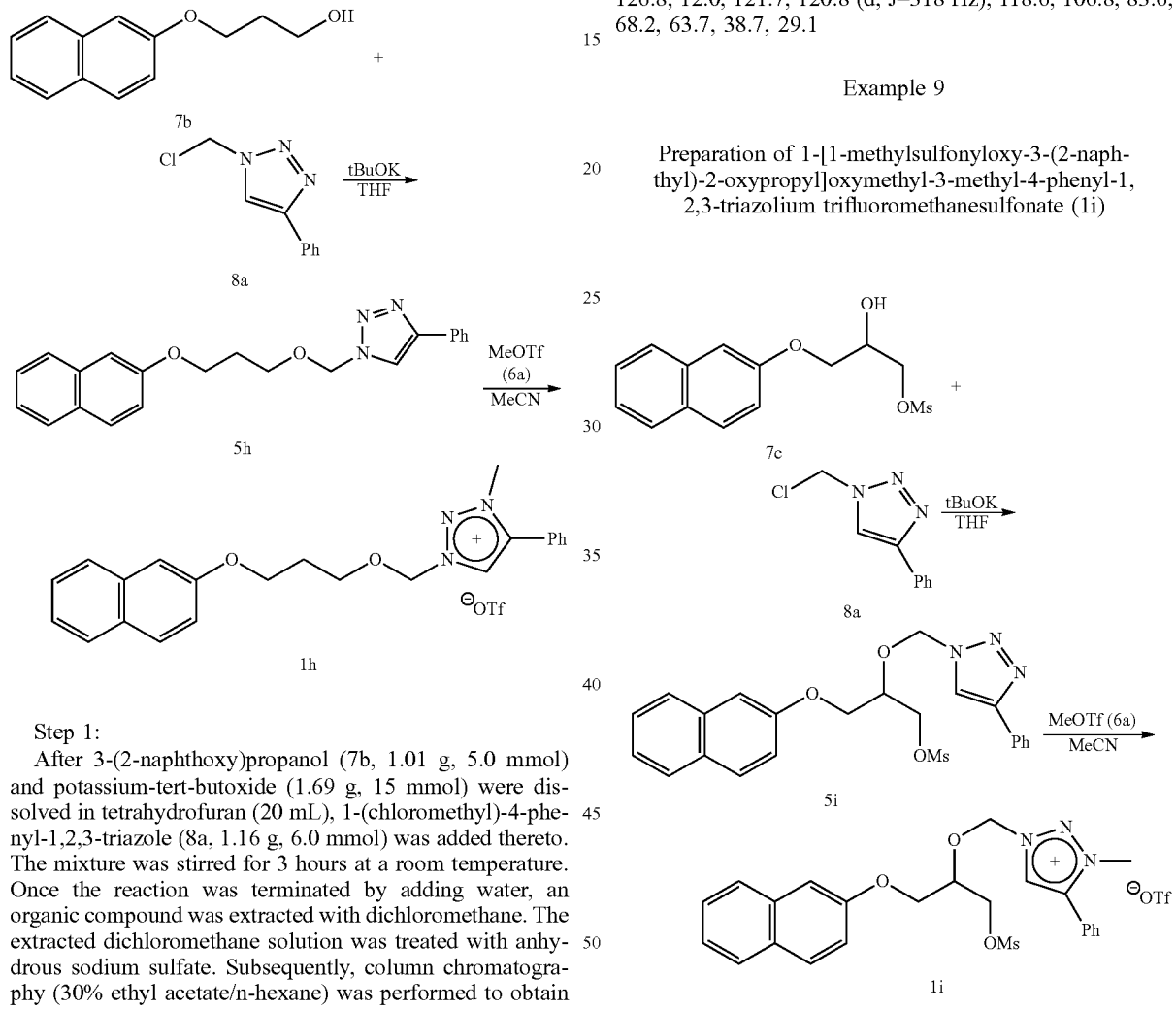

Step 1:

After 3-(2-naphthoxy)propanol (7b, 1.01 g, 5.0 mmol) and potassium-tert-butoxide (1.69 g, 15 mmol) were dissolved in tetrahydrofuran (20 mL), 1-(chloromethyl)-4-phenyl-1,2,3-triazole (8a, 1.16 g, 6.0 mmol) was added thereto. The mixture was stirred for 3 hours at a room temperature. Once the reaction was terminated by adding water, an organic compound was extracted with dichloromethane. The extracted dichloromethane solution was treated with anhydrous sodium sulfate. Subsequently, column chromatography (30% ethyl acetate/n-hexane) was performed to obtain a desired compound, 1-[3-(2-naphthoxy)-n-propyl]oxymethyl-4-phenyl-1,2,3-triazole (5h, 1.25 g, 70%).

$^1$H NMR (500 MHz, CDCl$_3$) δ 2.10 (q, J=6.0 Hz, 2H), 3.79 (t, J=6.3 Hz, 2H), 4.12 (t, J=6.3 Hz, 2H), 5.74 (s, 2H), 7.05 (dd, J=9.0 Hz, J=2.5 Hz, 1H), 7.09 (d, J=2.5 Hz, 1H), 7.38-7.31 (m, 4H), 7.44-7.41 (m, 1H), 7.65 (d, J=8.5 Hz, 1H), 7.68 (d, J=8.5 Hz, 1H), 7.76-7.73 (m, 3H), 7.87 (s, 1H);

$^{13}$C NMR (125 MHz, CDCl$_3$) δ 156.9, 148.9, 134.7, 130.4, 129.6, 129.2, 129.0, 128.5, 127.8, 126.9, 126.5, 126.0, 123.8, 119.3, 118.9, 106.8, 79.3, 66.5, 64.2, 29.3.

Step 2:

After 1-[3-(2-naphthoxy)-n-propyl]oxymethyl-4-phenyl-1,2,3-triazole (5h, 1.25 mg, 3.5 mmol) obtained in step 1 was dissolved in acetonitrile (14.0 mL), methyl trifluoromethanesulfonate (6a, MeOTf, 0.57 mL, 5.25 mmol) was added thereto. The mixture was stirred for 30 minutes at a 0° C., and then, the solvent was removed under a reduced pressure to obtain a desired compound, 3-methyl-1-[3-(2-naphthoxy)-n-propyl]oxymethyl-4-phenyl-1,2,3-trizaolium trifluoromethanesulfonate (1h, 1.4 g, 76%).

$^1$H NMR (500 MHz, CDCl$_3$) δ 2.11 (q, J=5.8 Hz, 2H), 4.01-3.99 (m, 5H), 4.08 (t, J=5.5 Hz, 2H), 5.95 (s, 2H), 7.01 (dd, J=9.0, 2.5 Hz, 1H), 7.07 (d, J=2.5 Hz, 1H), 7.44-7.26 (m, 7H), 7.51-7.48 (m, 1H), 7.62 (d, J=9.0 Hz, 1H), 7.67 (d, J=8.0 Hz, 1H), 7.71 (d, J=8.0 Hz, 1H), 8.68 (s, 1H);

$^{13}$C NMR (125 MHz, CDCl$_3$) δ 156.7, 143.8, 134.7, 132.0, 129.71, 129.66, 129.5, 129.1, 128.3, 127.8, 126.9, 126.8, 12.0, 121.7, 120.8 (d, J=318 Hz), 118.6, 106.8, 83.6, 68.2, 63.7, 38.7, 29.1

Example 9

Preparation of 1-[1-methylsulfonyloxy-3-(2-naphthyl)-2-oxypropyl]oxymethyl-3-methyl-4-phenyl-1,2,3-triazolium trifluoromethanesulfonate (1i)

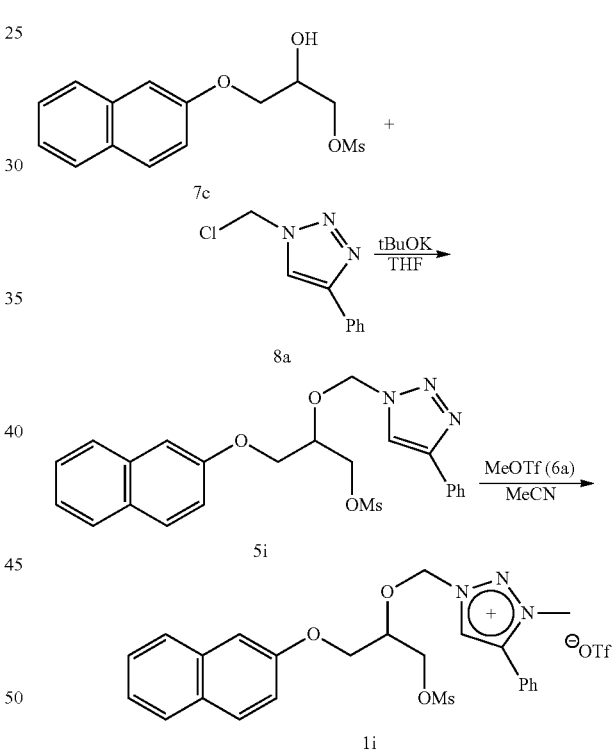

1-[1-Methylsulfonyloxy-3-(2-naphthyl)-2-oxypropyl]oxymethyl-3-methyl-4-phenyl-1,2,3-triazolium trifluoromethanesulfonate (1i, 1.39 g, 75%) was obtained in the same manner as used in Example 8, except that 2-hydroxy-3-(2-naphthalenyloxy)propylmethanesulfonate (7c, 889 mg, 3.0 mmol) was used, instead of 3-(2-naphthoxy)propanol (7b) of Example 8.

$^1$H NMR (500 MHz, CDCl$_3$) δ 2.99 (s, 3H), 4.15 (s, 3H), 4.31-4.22 (m, 2H), 4.43 (d, J=5.5 Hz, 2H), 4.69-4.67 (m, 1H), 6.22 (q, J=9.3 Hz, 2H), 7.07 (dd, J=8.8, 2.8 Hz, 1H), 7.13 (d, J=2.5 Hz, 1H), 7.43 (td, J=7.5 Hz, 1.0 Hz, 1H), 7.52-7.48 (m, 4H), 7.57-7.54 (m, 1H), 7.69 (d, J=9.0 Hz, 2H), 7.23 (t, J=8.0 Hz, 2H), 8.91 (s, 1H);

$^{13}$C NMR (125 MHz, CDCl$_3$) δ 155.9, 143.9, 134.5, 132.1, 129.9, 129.8, 129.6, 129.5, 128.8, 127.8, 127.2, 126.9, 124.4, 122.0, 120.9 (d, J=319 Hz), 118.3, 107.5, 82.8, 78.5, 69.7, 67.2, 38.8, 37.4

Example 10

Preparation of 3-methyl-(2-naphthyl)methyloxymethyl-4-phenyl-1,2,3-triazolium trifluoromethanesulfonate (1j)

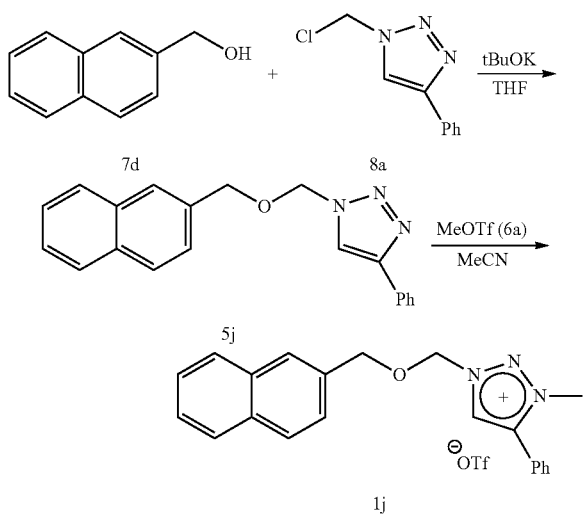

3-Methyl-(2-naphthyl)methyloxylmethyl-4-phenyl-1,2,3-triazolium trifluoromethanesulfonate (1j, 1.09 g, 76%) was obtained in the same manner as used in Example 8, except that naphthalenemethanol (7d, 475 mg, 3.0 mmol) was used, instead of 3-(2-naphthoxy)propanol (7b) of Example 8.

$^1$H NMR (500 MHz, CDCl$_3$) δ 3.96 (s, 3H), 4.88 (s, 2H), 5.94 (s, 2H), 7.24 (d, J=7.5 Hz, 2H), 7.45-7.32 (m, 6H), 7.68 (d, J=8.5 Hz, 1H), 7.76-7.71 (m, 3H), 8.48 (s, 1H);

$^{13}$C NMR (125 MHz, CDCl$_3$) δ 143.39, 143.38, 133.1, 132.9, 131.8, 129.5, 129.3, 128.3, 128.2, 128.1, 127.69, 127.67, 126.61, 126.55, 125.9, 124.6, 121.59, 121.58, 120.8 (q, J=319 Hz), 82.7, 73.9, 38.5

Example 11

Preparation of (s)-1-[4-[2-BOC-amino-2-(t-butoxycarbonyl) ethyl]phenyloxymethyl]-3-methyl-4-phenyl-1,2,3-triazolium trifluoromethanesulfonate (1k)

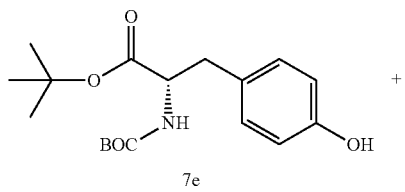

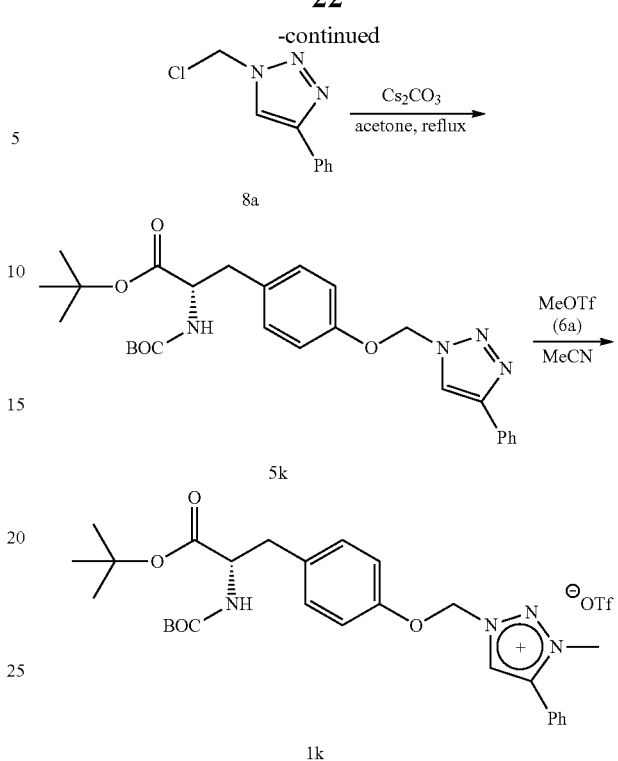

Step 1:

After N—BOC-L-tyrosine tert-butyl ester (7e, 0.79 g, 2.35 mmol) was dissolved in acetone (23 mL), cesium carbonate (2.00 g, 5.87 mmol) and 1-(chloromethyl)-4-phenyl-1,2,3-triazole (8a, 0.46 g, 2.59 mmol) were added thereto in sequence. The mixture was stirred for 6 hours at 50° C. The reactant was distillated under a reduced pressure, diluted with ethyl acetate, and then, filtered. The filtrate was washed with a 1.0N aqueous HCl solution, water and a saturated aqueous sodium chloride solution in this order. The washed organic layer was dried with anhydrous sodium sulfate, and then, concentrated. Subsequently, column chromatography (SiO$_2$, 20% ethyl acetate/n-hexane) was performed to obtain a compound of white solid, (s)-1-(4-(2-BOC-amino-2-(t-butoxycarbonyl)ethyl)phenylmethyl)-4-phenyl-1,2,3-triazole (5k, 1.07 g, 2.16 mmol, 92%).

$^1$H NMR (400 MHz, CDCl$_3$) δ 1.38 (s, 18H), 2.99 (s, 2H), 4.39 (d, J=6.4 Hz, 1H), 5.03 (d, J=8 Hz, 1H), 6.23 (s, 3H), 7.09 (d, J=8 Hz, 2H), 7.33 (d, J=6.4 Hz, 1H), 7.41 (t, J=7.6 Hz, 1H), 7.82 (d, J=7.6 Hz, 2H), 7.97 (s, 1H)

Step 2:

After (s)-1-[4-[2-BOC-amino-2-(t-butoxycarbonyl)ethyl] phenyloxymethyl]-4-phenyl-1,2,3-triazole (5k, 0.47 g, 0.96 mmol) obtained in step 1 was dissolved in acetonitrile (2.5 mL), methyl trifluoromethanesulfonate (6a, 53 μL, 0.48 mmol) was added thereto. The mixture was stirred for 90 minutes at a room temperature. The reactant was concentrated. Subsequently, column chromatography (SiO$_2$, 5% methanol/dichloromethane) was performed to obtain a desired compound, (s)-1-[4-[2-BOC-amino-2-(t-butoxycarbonyl)ethyl]phenyloxymethyl]-3-methyl-4-phenyl-1,2,3-triazolium trifluoromethanesulfonate (1k, 0.22 g, 0.34 mmol, 70%).

$^1$H NMR (400 MHz, CDCl$_3$) δ 1.40 (s, 18H), 3.04-2.98 (m, 2H), 4.30 (s, 3H) 4.37 (d, J=6.0 Hz, 1H), 5.00 (d, J=8.0 Hz, 1H), 6.54 (s, 2H), 7.03 (d, J=8.8 Hz, 1H), 7.14 (d, J=8.4 Hz, 2H), 7.61-7.54 (m, 5H), 8.70 (s, 1H)

Example 12

Preparation of 3-methyl-1-[(2-naphthoxy)methyl]-4-phenylimidazolium trifluoromethanesulfonate (11)

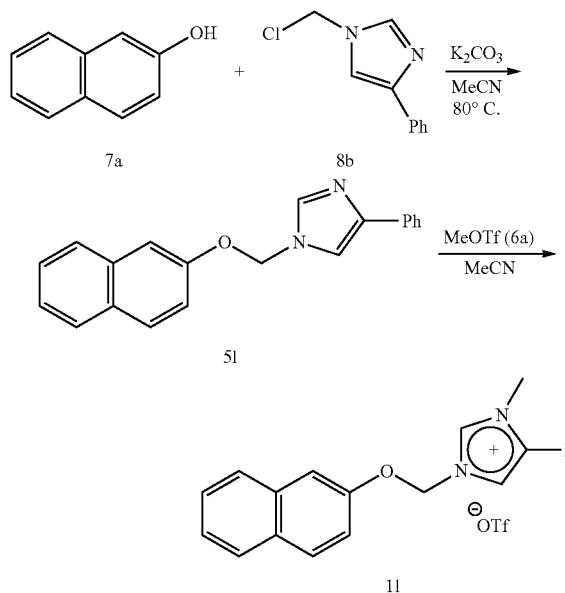

Step 1:

After 2-naphthol (7a, 720 mg, 5.0 mmol) and potassium carbonate (2.07 g, 15 mmol) were dissolved in acetonitrile (20 mL), 1-(chloromethyl)-4-phenyl-imidazole (8b, 1.44 g, 7.5 mmol) was added thereto. The mixture was stirred for 5 hours at the heating condition of 80° C. Once the reaction was terminated by adding water, an organic compound was extracted with ethyl acetate. The extracted ethyl acetate solution was treated with anhydrous sodium sulfate. Subsequently, column chromatography (20% ethyl acetate/n-hexane) was performed to obtain a desired compound, 4-phenyl-1-[(2-naphthoxy)methyl]imidazole (51, 931 mg, 62%).

$^1$H NMR (500 MHz, CDCl$_3$) δ 5.94 (s, 2H), 7.13 (dd, J=9.2 Hz, J=2.4 Hz, 1H), 7.28-7.24 (m, 2H), 7.43-7.36 (m, 4H), 7.48 (td, J=7.4 Hz, J=1.2 Hz, 1H), 7.71 (d, J=1.2 Hz, 1H), 7.74 (d, J=8.0 Hz, 1H), 7.81-7.77 (m, 4H)

Step 2:

After 4-phenyl-1-[(2-naphthoxy)methyl]imidazole (51, 931 mg, 3.10 mmol) obtained in step 1 was dissolved in acetonitrile (15 mL), methyl trifluoromethanesulfonate (6a, MeOTf, 0.51 mL, 4.65 mmol) was added thereto. The mixture was stirred for 30 minutes at 0° C., and then, the solvent was removed under a reduced pressure to obtain a desired compound, 4-phenyl-3-methyl-1-[(2-naphthoxy)methyl]-imidazolium trifluoromethanesulfonate (11, 734 mg, 51%).

$^1$H NMR (500 MHz, CDCl$_3$) δ 3.78 (s, 3H), 6.33 (s, 2H), 7.21 (dd, J=8.8, 2.3 Hz, 1H), 7.38-7.34 (m, 3H), 7.52-7.41 (m, 6H), 7.73 (d, J=8.0 Hz, 1H), 7.76 (d, J=9.0 Hz, 1H), 7.84 (d, J=8.0 Hz, 1H), 9.57 (s, 1H);

$^{13}$C NMR (125 MHz, CDCl$_3$) δ 152.9, 138.1, 136.5, 134.3, 131.1, 130.6, 130.3, 129.6, 129.5, 127.72, 127.69, 127.1, 125.2, 124.5, 120.9 (q, J=319 Hz), 118.5, 118.2, 110.3, 76.0, 35.1

Example 13

Preparation of 3-methyl-1-[(2-naphthoxy)methyl]-4-phenyl-1,2,3-triazolium trifluoromethanesulfonate (1g)

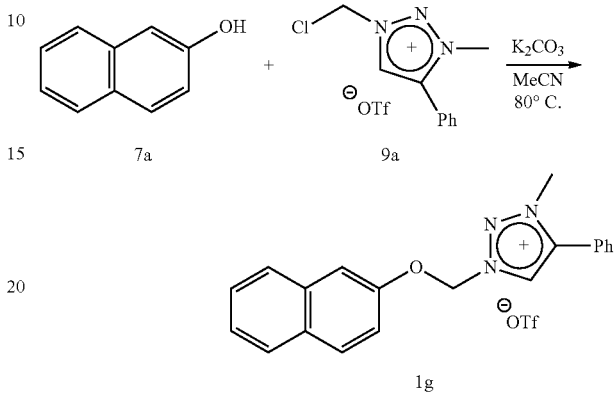

After 2-naphthol (7a, 288 mg, 2.0 mmol) and potassium carbonate (829 mg, 6.0 mmol) were dissolved in acetonitrile (8 mL), 1-(chloromethyl)-4-phenyl-3-methyl-1,2,3-triazolium trifluoromethanesulfonate (9a, 858 mg, 2.4 mmol) was added thereto. The mixture was stirred for 5 hours at the heating condition of 80° C. Once the reaction was terminated by adding water, an organic compound was extracted with dichloromethane. The extracted dichloromethane solution was treated with anhydrous sodium sulfate. Subsequently, column chromatography (5% methanol/dichloromethane) was performed to obtain the same desired compound as that in Example 7, i.e., 4-phenyl-3-methyl-1-[(2-naphthoxy)methyl]-1,2,3-triazolium trifluoromethanesulfonate (1g, 577 mg, 62%).

$^1$H NMR (500 MHz, CDCl$_3$) δ 3.81 (s, 3H), 6.35 (s, 2H), 7.22 (dd, J=9.0 Hz, 2.0 Hz, 1H), 7.40-7.35 (m, 3H), 7.54-7.43 (m, 6H), 7.75 (d, J=8.0 Hz, 1H), 7.78 (d, J=9.0 Hz, 1H), 7.85 (t, J=8.5 Hz, 1H), 9.63 (s, 1H);

$^{13}$C NMR (125 MHz, CDCl$_3$) δ 152.8, 138.3, 136.6, 134.3, 131.1, 130.6, 130.4, 129.64, 129.60, 127.7, 127.2, 125.3, 124.5, 120.9 (d, J=319), 118.4, 118.1, 110.3, 76.0, 35.1

Example 14

Preparation of 1-(4-biphenyl)oxymethyl-3-methyl-4-phenyl-1,2,3-triazolium trifluoromethanesulfonate (1m)

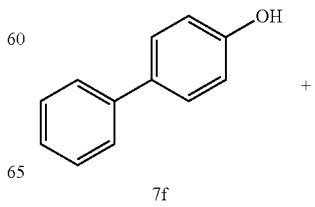

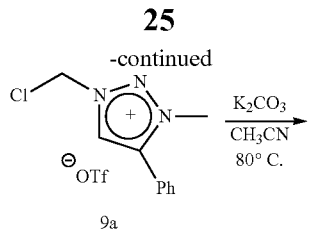

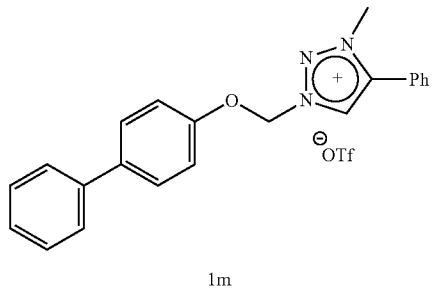

1-(4-Biphenyl)oxymethyl-3-methyl-4-phenyl-1,2,3-triazolium trifluoromethanesulfonate (1m, 1.28 g, 87%) was obtained in the same manner as used in Example 12, except that 4-phenylphenol (7f, 510 mg, 3.0 mmol) was used, instead of 2-naphthol (7a) of Example 12.

$^1$H NMR (500 MHz, CDCl$_3$) δ 4.26 (s, 3H), 6.56 (s, 2H), 7.19 (q, J=5.0 Hz, 1H), 7.19 (d, J=9.0 Hz, 1H), 7.32 (td, J=7.5, 1.3 Hz, 1H), 7.41 (t, J=7.8 Hz, 2H), 7.61-7.50 (m, 9H), 7.80 (t, J=8.5 Hz, 2H), 8.79 (s, 1H);

$^{13}$C NMR (125 MHz, CDCl$_3$) δ 154.8, 144.0, 140.0, 137.4, 132.3, 129.9, 129.7, 129.0, 128.9, 128.8, 127, 121.7, 120.8 (q, J=319 Hz), 116.6, 79.7, 39.1

Example 15

Preparation of 1-(4-bromo-2-methylphenyl)oxymethyl-3-methyl-4-phenyl-1,2,3-triazolium trifluoromethanesulfonate (1n)

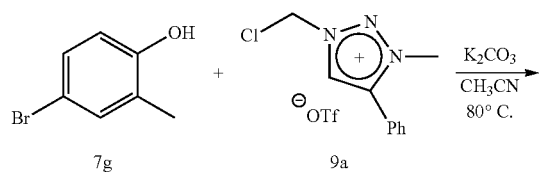

1-(4-Bromo-2-methylphenyl)oxymethyl-3-methyl-4-phenyl-1,2,3-triazolium trifluoromethanesulfonate (1n, 1.14 g, 75%) was obtained in the same manner as used in Example 12, except that 4-bromo-2-methylphenol (7g, 561 mg, 3.0 mmol) was used, instead of 2-naphthol (7a) of Example 12.

$^1$H NMR (500 MHz, CDCl$_3$) δ 2.20 (s, 3H), 4.28 (s, 3H), 7.04 (d, J=9.5 Hz, 2H), 7.31-7.27 (m, 2H), 7.61-7.53 (m, 5H), 8.83 (s, 1H);

$^{13}$C NMR (125 MHz, CDCl$_3$) δ 152.8, 144.0, 134.5, 132.3, 130.5, 130.4, 129.9, 129.7, 128.9, 121.7, 120.7 (q, J=319 Hz), 116.6, 115.3, 79.6, 39.1, 16.1

Example 16

Preparation of 1-(3,4-dimethoxyphenyl)oxymethyl-3-methyl-4-phenyl-1,2,3-triazolium trifluoromethanesulfonate (1o)

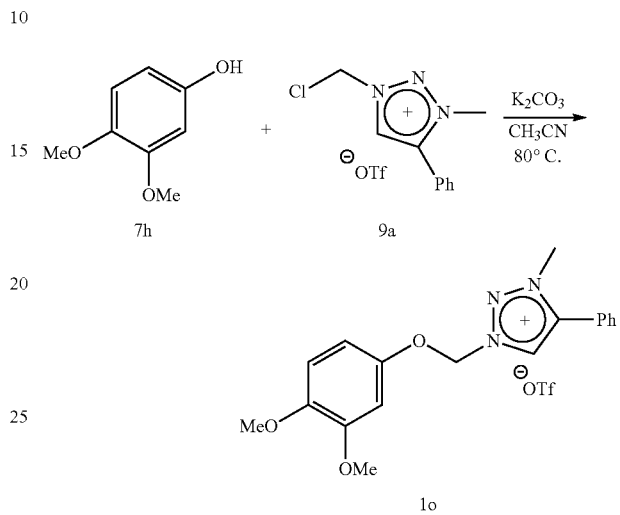

1-(3,4-Dimethoxyphenyl)oxymethyl-3-methyl-4-phenyl-1,2,3-triazolium trifluoromethanesulfonate (1o, 927 mg, 65%) was obtained in the same manner as used in Example 12, except that 3,4-dimethoxyphenol (7h, 462 mg, 3.0 mmol) was used, instead of 2-naphthol (7a) of Example 12.

$^1$H NMR (500 MHz, CDCl$_3$) δ 3.79 (s, 3H), 3.82 (s, 3H), 4.24 (s, 3H), 6.43 (s, 2H), 6.62 (dd, J=8.5, 2.8 Hz, 1H), 6.68 (s, 1H), 6.76 (d, J=8.5 Hz, 1H), 7.58-7.48 (m, 5H), 8.72 (s, 1H);

$^{13}$C NMR (125 MHz, CDCl$_3$) δ 105.2, 149.4, 146.0, 143.8, 132.2, 129.8, 129.5, 128.6, 121.7, 120.7 (q, J=319 Hz), 111.7, 106.8, 102.4, 80.6, 56.3, 56.2, 39.0

Example 17

Preparation of 3-methyl-1-(4-nitrophenyl)oxymethyl-4-phenyl-1,2,3-triazolium trifluoromethanesulfonate (1p)

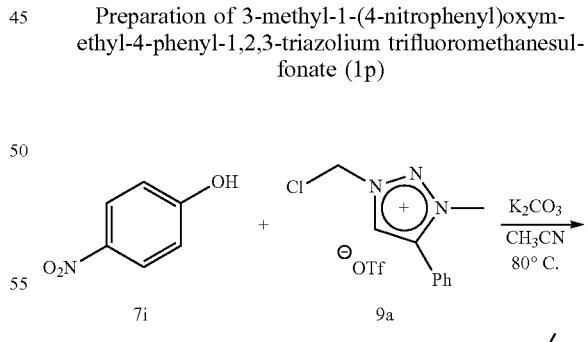

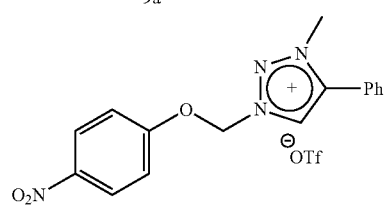

3-Methyl-1-(4-nitrophenyl)oxymethyl-4-phenyl-1,2,3-triazolium trifluoromethanesulfonate (1p, 898 mg, 65%) was obtained in the same manner as used in Example 12, except that 4-nitrophenol (71,417 mg, 3.0 mmol) was used, instead of 2-naphthol (7a) of Example 12.

$^1$H NMR (500 MHz, CDCl$_3$) δ 4.36 (s, 3H), 6.79 (s, 2H), 7.41 (d, J=9.5 Hz, 2H), 7.72-7.64 (m, 5H), 8.30 (d, J=9.5 Hz, 2H);

$^{13}$C NMR (125 MHz, CDCl$_3$) δ 160.1, 144.2, 143.8, 131.8, 129.4, 129.2, 125.7, 122.1, 120.4 (d, J=317 Hz, only two peaks of quartet of CF$_3$—C were shown), 116.3, 78.5, 38.3.

Example 18

Preparation of 1-(3-acetylaminophenyl)oxymethyl-3-methyl-4-phenyl-1,2,3-triazolium trifluoromethanesulfonate (1q)

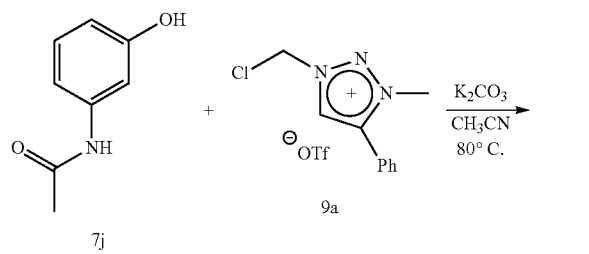

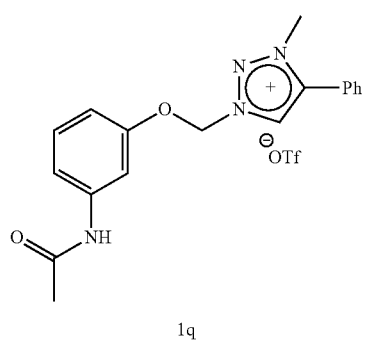

1-(3-Acetylaminophenyl)oxymethyl-3-methyl-4-phenyl-1,2,3-triazolium trifluoromethanesulfonate (1q, 1.08 g, 76%) was obtained in the same manner as used in Example 12, except that 3-acetaminophenol (7j, 453 mg, 3.0 mmol) was used, instead of 2-naphthol (7a) of Example 12.

$^1$H NMR (500 MHz, CDCl$_3$) δ 2.09 (s, 3H), 6.41 (s, 2H) 4.26 (s, 3H), 6.72 (dd, J=8.3, 2.3 Hz, 1H), 7.20-7.15 (m, 2H), 7.63-7.49 (m, 5H), 7.66 (d, J=8.0 Hz, 1H), 8.70 (s, 1H), 8.93 (s, 1H);

$^{13}$C NMR (125 MHz, CDCl$_3$) δ 170.0, 155.4, 144.1, 140.9, 132.5, 130.8, 130.0, 129.7, 128.3, 121.7, 120.7 (q, J=318 Hz), 116.0, 112.5, 106.6, 80.1, 39.2, 24.5

Example 19

Preparation of 1-(3-O-estronyl)methyl-3-methyl-4-phenyl-1,2,3-triazolium trifluoromethanesulfonate (1r)

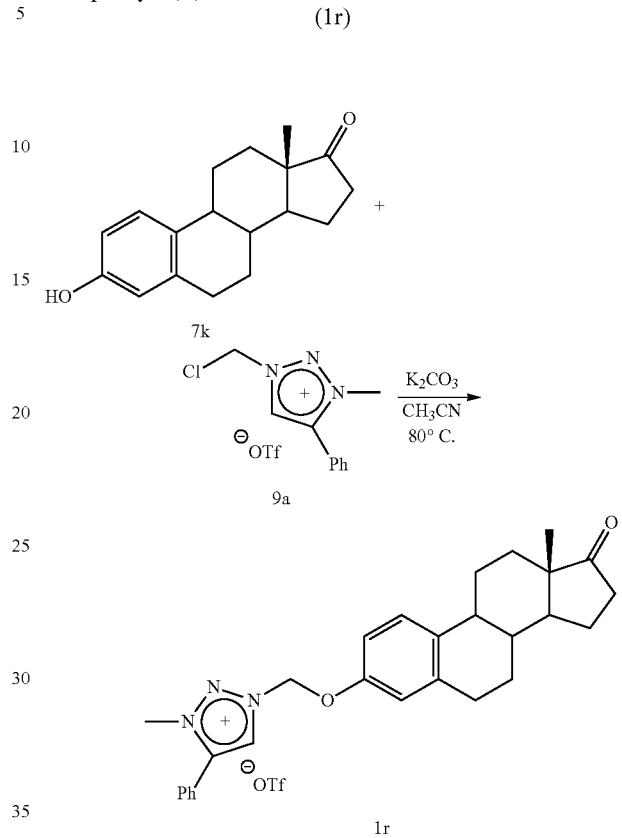

1-(3-O-Estronyl)methyl-3-methyl-4-phenyl-1,2,3-triazolium trifluoromethanesulfonate (1r, 1.26 g, 71%) was obtained in the same manner as used in Example 12, except that estrone (7k, 811 mg, 3.0 mmol) was used, instead of 2-naphthol (7a) of Example 12.

$^1$H NMR (500 MHz, CDCl$_3$) δ 0.89 (s, 3H), 1.64-1.39 (m, 6H), 1.95-1.93 (m, 1H), 2.16-1.98 (m, 4H), 2.24-2.20 (m, 1H), 2.37-2.35 (m, 1H), 2.49 (dd, J=19.0, 8.5 Hz, 2H), 2.92-2.90 (m, 2H), 4.27 (s, 3H), 6.50 (s, 2H), 6.88-6.87 (m, 2H), 7.24 (d, J=9.5 Hz, 1H), 7.62-7.55 (m, 5H), 8.70 (s, 1H);

$^{13}$C NMR (125 MHz, CDCl$_3$) δ 220.7, 153.5, 144.0, 139.1, 136.1, 132.3, 129.9, 129.7, 128.7, 127.2, 121.8, 120.8 (q, J=319 Hz), 116.3, 113.5, 80.0, 50.6, 48.1, 44.2, 39.0, 38.3, 36.0, 31.7, 29.6, 26.5, 26.0, 21.7, 14.0

Example 20

Preparation of 3-acetonaphthyl-1-methylimidazolium (1s)

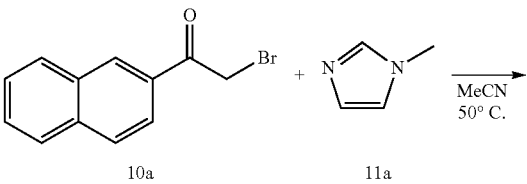

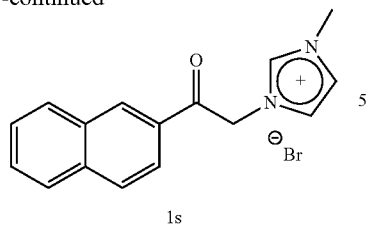

1s

After 2-bromo-2-acetonaphthone (10a, 2.49 g, 10 mmol) was dissolved in acetonitrile (50 mL), methylimidazole (11a, 0.836 mL, 10.5 mmol) was added thereto. The mixture was stirred for 12 hours in the heating condition of 50° C. Once the reaction was terminated, the reaction solvent was removed under a reduced pressure. Subsequently, column chromatography (10% methanol/dichloromethane) was performed to obtain a desired compound, 3-acetonaphthyl-1-methylimidazolium (1s, 3.08 g, 93%).

$^1$H NMR (500 MHz, CDCl$_3$) δ 4.02 (s, 3H), 6.15 (s, 2H), 7.68 (m, 4H), 7.99 (m, 4H), 8.74 (s, 1H), 9.01 (s, 1H);

$^{13}$C NMR (125 MHz, CDCl$_3$) δ 191.3, 139.5, 137.7, 134.0, 132.5, 130.9, 130.5, 130.0, 129.4, 129.0, 128.7, 125.4, 124.6, 124.3, 56.3, 36.8

Example 21

Nucleophilic Fluorination Reaction

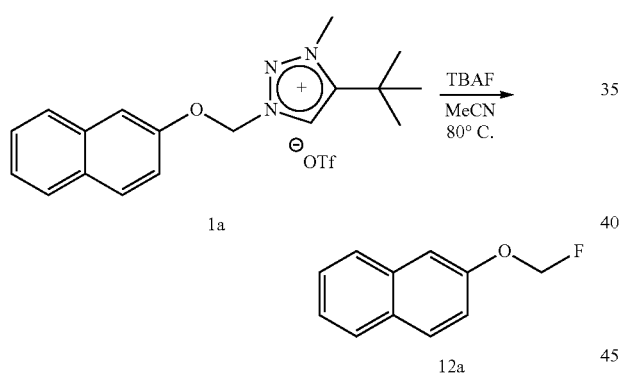

4-Tert-butyl-3-methyl-1-[(2-naphthoxy)methyl]-1,2,3-triazolium trifluoromethanesulfonate (1a, 0.5 mmol) obtained in Example 1 and tetrabutylammonium fluoride (TBAF, 0.75 mmol) were placed in a reaction vessel, and acetonitrile (2.0 mL) was added thereto to dissolve the mixture. The mixture was stirred for 1 hour in the heating condition of 80° C. Once the reaction was terminated by adding water, an organic compound was extracted with dichloromethane. The extracted dichloromethane solution was treated with anhydrous sodium sulfate. Subsequently, column chromatography (2% ethyl acetate/hexane) was performed to obtain a desired compound, 2-fluoromethoxy naphthalene (12a, 78 mg, 89%).

$^1$H NMR (500 MHz, CDCl$_3$) δ 5.85 (d, J=55.0 Hz, 2H), 7.29 (dd, J=9.0, 2.5 Hz, 1H), 7.44 (t, J=7.3 Hz, 1H), 7.52-7.49 (m, 2H), 7.81 (d, J=8.5 Hz, 1H), 7.83 (d, J=9.0 Hz, 2H);

$^{13}$C NMR (125 MHz, CDCl$_3$) δ 154.9, 134.5, 130.5, 130.1, 128.0, 127.6, 126.9, 125.1, 118.8, 111.4, 101.1 (d, J=218 Hz)

Example 22

Fluorination Reactions Under the Condition of Various Organic Solvents

Fluorination reactions were conducted in the same manner as used in Example 20 while using 4-tert-butyl-3-methyl-1-[(2-naphthoxy)methyl]-1,2,3-triazolium trifluoromethanesulfonate (1a, 0.5 mmol) obtained in Example 1, tetrabutylammonium fluoride (TBAF, 196 mg, 0.75 mmol), and various organic solvents (2.0 mL) such as tert-butanol, tetrahydrofuran and dimethylformamide, instead of acetonitrile. The reaction time for each of the reactions was checked. A yield of 2-fluoromethoxynaphthalene, which is a resulting product from a fluorination reaction, was measured. The following Table 1 shows the measurement results.

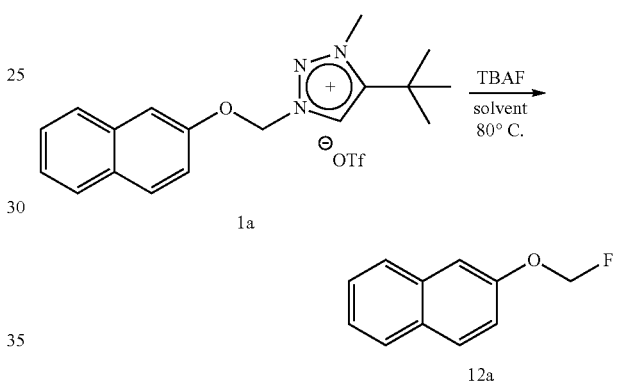

TABLE 1

| Solvent | Time (min) | Yield (%) |
|---------|------------|-----------|
| MeCN    | 60         | 89        |
| t-BuOH  | 60         | 81        |
| THF     | 40         | 85        |
| DMF     | 20         | 79        |

Example 23

Reactions Using Various Fluorination Reagents

Fluorination reactions were conducted in the same manner as used Example 21 while using 4-tert-butyl-3-methyl-1-[(2-naphthoxy)methyl]-1,2,3-triazolium trifluoromethanesulfonate (1a, 0.5 mmol) obtained in Example 1 and cesium fluoride as a fluorination reagent, instead of tetrabutylammonium fluoride. The reaction time for each of the reactions was checked. A yield of 2-fluoromethoxynaphthalene, which is a resulting product from a fluorination reaction, was measured. The following Table 2 shows the measurement results.

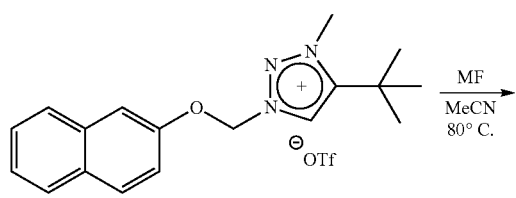

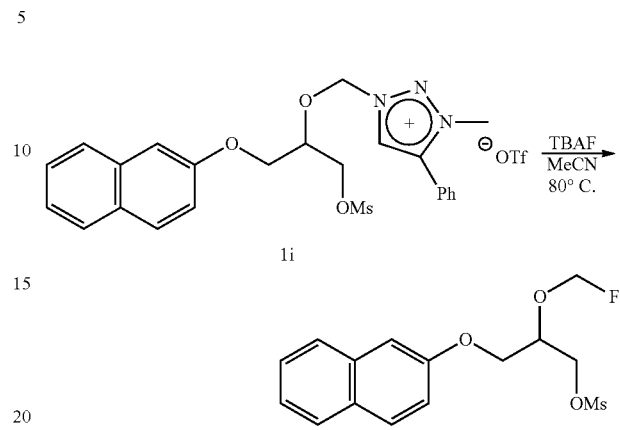

Example 25

Preparation of 2-(2-fluoromethoxy-3-methanesulfonyloxy-n-propoxy)naphthalene (12c)

2-(2-Fluoromethoxy-3-methanesulfonyloxy-n-propoxy)naphthalene (12c, 110 mg, 67%) was obtained in the same manner as used in Example 21, except that 1-[1-methylsulfonyloxy-3-(2-naphthyl)-2-oxypropyl]oxymethyl-3-methyl-4-phenyl-1,2,3-triazolium trifluoromethanesulfonate (1i, 310 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 3.06 (s, 3H), 4.37-4.23 (m, 3H), 4.58-4.49 (m, 2H), 5.46 (ddd, J=55.8, 17.5, 3.0 Hz, 2H), 7.16-7.14 (m, 2H), 7.37 (td, J=8.0, 1.0 Hz, 1H), 7.47 (td, J=8.3, 1.3 Hz, 1H), 7.76 (q, J=9.00 Hz, 3H);

$^{13}$C NMR (125 MHz, CDCl$_3$) δ 156.1, 134.6, 130.0, 129.5, 127.9, 127.1, 126.9, 124.4, 118.7, 107.2, 103.8 (d, J=216 Hz), 69.1, 67.0, 37.8

TABLE 2

| MF (equivalent) | Time | Yield (%) |
| --- | --- | --- |
| CsF (3.0) | 24 h | 38 |
| TBAF (1.5) | 60 min | 89 |

Example 24

Preparation of 2-(3-fluoromethoxy-n-propoxy)naphthalene (12b)

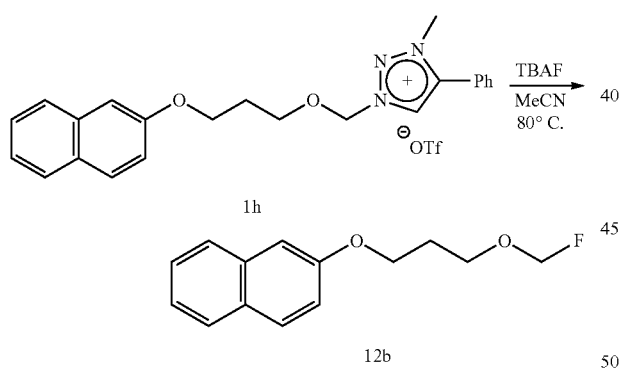

2-(3-Fluoromethoxy-n-propoxy)naphthalene (12b, 90 mg, 77%) was obtained in the same manner as used in Example 21, except that 3-methyl-1-[3-(2-naphthoxy)-n-propyl]oxymethyl-4-phenyl-1,2,3-triazolium trifluoromethanesulfonate (1h, 262 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 2.19 (q, J=6.1 Hz, 2H), 3.98 (td, J=6.3, 2.0 Hz, 2H), 4.21 (t, J=6.0 Hz, 2H), 5.30 (d, J=56.0 Hz, 2H), 7.16-7.14 (m, 2H), 7.34 (td, J=7.5, 1.2 Hz, 1H), 7.45 (td, J=7.5, 2.0 Hz, 1H), 7.78-7.72 (m, 3H);

$^{13}$C NMR (125 MHz, CDCl$_3$) δ 154.9, 134.5, 130.5, 130.1, 128.0, 127.6, 126.9, 125.1, 118.8, 111.4, 101.1 (d, J=218 Hz)

Example 26

Preparation of (2-fluoromethoxy)-2-methylnaphthalene (12d)

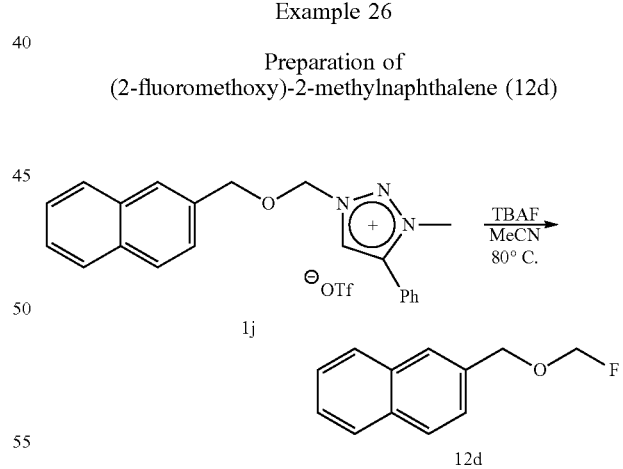

(2-Fluoromethoxy)-2-methylnaphthalene (12d, 75 mg, 79%) was obtained in the same manner as used in Example 21, except that 3-methyl-(2-naphthyl)methyloxymethyl-4-phenyl-1,2,3-triazolium trifluoromethanesulfonate (1j, 240 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 4.95 (s, 2H), 5.40 (d, J=56.4 Hz, 2H), 7.75 Hz, 2H), 7.51-7.47 (m, 3H), 7.87-7.83 (m, 4H);

$^{13}$C NMR (125 MHz, CDCl$_3$) δ 134.0, 133.4, 133.3, 128.6, 128.1, 127.9, 127.2, 126.5, 126.4, 125.9, 102.9 (d, J=213 Hz), 72.0

Example 27

Preparation of O-fluoromethyl-N—BOC-L-tyrosine-tert-butyl ester (12e)

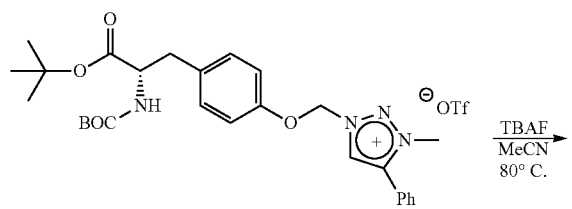

O-Fluoromethyl-N—BOC-L-tyrosine-tert-butyl ester (12e, 75 mg, 60%) was obtained in the same manner as used in Example 21, except that (s)-1-[4-[2-BOC-amino-2-(t-butoxycarbonyl)ethyl]phenyloxymethyl]-3-methyl-4-phenyl-1,2,3-triazolium trifluoromethanesulfonate (1k, 0.22 g, 0.36 mmol) was used, instead of 4-tert-butyl-3-methyl-1-[(2-naphthoxy)methyl]-1,2,3-triazolium trifluoromethanesulfonate (1a) of Example 21.

$^1$H NMR (400 MHz, CDCl$_3$) δ 1.42 (d, J=4.0 Hz, 18H), 3.01-3.04 (m, 2H), 4.42 (d, J=6.8 Hz, 1H), 4.98 (d, J=6.8 Hz, 1H), 5.62 (s, 1H), 5.76 (s, 1H), 7.00 (d, J=8.4 Hz, 2H), 7.13 (d, J=8.4 Hz, 2H)

Example 28

Preparation of 4-fluoromethoxy biphenyl (12f)

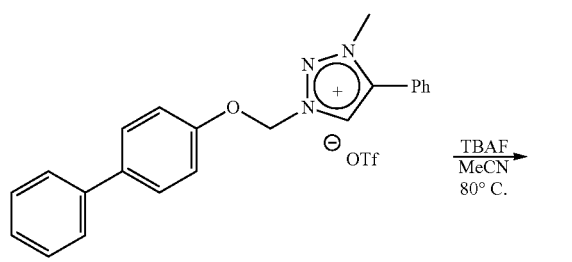

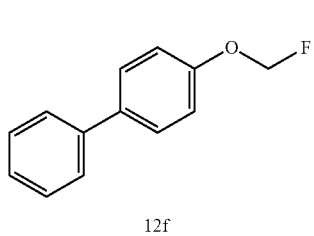

4-Fluoromethoxy biphenyl (12f, 74 mg, 73%) was obtained in the same manner as used in Example 21, except that 1-(4-biphenyl)oxymethyl-3-methyl-4-phenyl-1,2,3-triazolium trifluoromethanesulfonate (1m, 246 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 5.78 (d, J=55.0 Hz, 2H), 7.21 (d, J=9.0 Hz, 2H), 7.39 (td, J=7.5, 1.0 Hz, 1H), 7.49 (t, J=7.8 Hz, 2H), 7.61 (d, J=8.5 Hz, 4H);

$^{13}$C NMR (125 MHz, CDCl$_3$) δ 156.59, 156.57, 140.7, 136.9, 129.1, 128.7, 127.4, 127.2, 117.23, 117.22, 101.0 (d, J=218 Hz)

Example 29

Preparation of 5-bromo-2-fluoromethoxytoluene (12g)

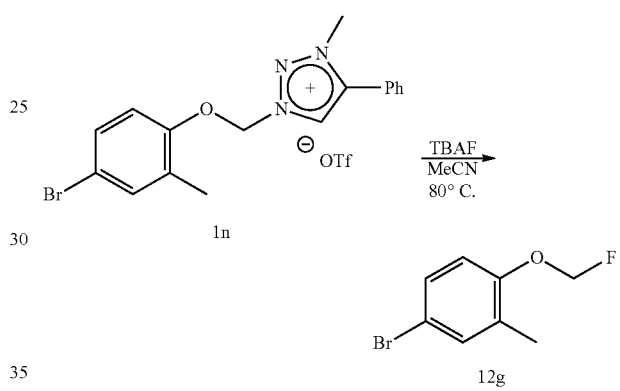

5-Bromo-2-fluoromethoxytoluene (12g, 91 mg, 83%) was obtained in the same manner as used in Example 21, except that 1-(4-bromo-2-methylphenyl)oxymethyl-3-methyl-4-phenyl-1,2,3-triazolium trifluoromethanesulfonate (1n, 254 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 2.24 (s, 3H), 5.70 (d, J=54.5 Hz, 2H), 6.95 (d, J=8.5 Hz, 1H) 7.31 (m, 2H);

$^{13}$C NMR (125 MHz, CDCl$_3$) δ 154.4, 133.9, 130.5, 130.0, 116.6, 116.0, 101.0 (d, J=218 Hz), 16.2

Example 30

Preparation of 4-fluoromethoxy-1,2-dimethoxybenzene (12h)

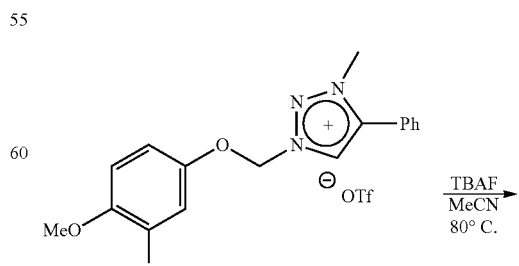

-continued

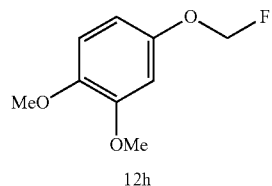

12h

4-Fluoromethoxy-1,2-dimethoxybenzene (12h, 70 mg, 75%) was obtained in the same manner as used in Example 21, except that 1-(3,4-dimethoxyphenyl)oxymethyl-3-methyl-4-phenyl-1,2,3-triazolium trifluoromethanesulfonate (1o, 238 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 3.84 (s, 3H), 3.85 (s, 3H), 5.64 (d, J=55.0 Hz, 2H), 6.65-6.61 (m, 2H), 6.78 (d, J=8.5 Hz, 1H);

$^{13}$C NMR (125 MHz, CDCl$_3$) δ 151.3, 149.8, 145.5, 111.6, 107.6, 102.6, 101.8 (d, J=217 Hz), 56.4, 56.0

Example 31

Preparation of 4-fluoromethoxy-1-nitrobenzene (12i)

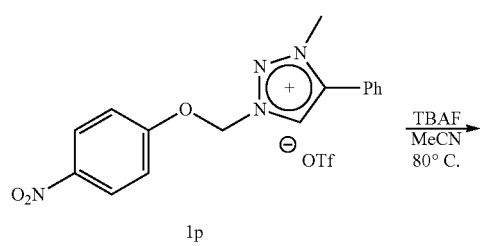

1p

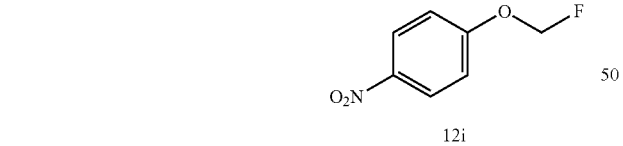

12i

4-Fluoromethoxy-1-nitrobenzene (12i, 62 mg, 72%) was obtained in the same manner as used in Example 21, except that 3-methyl-1-(4-nitrophenyl)oxymethyl-4-phenyl-1,2,3-triazolium trifluoromethanesulfonate (1p, 230 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 5.79 (d, J=53.0 Hz, 2H), 7.18-7.17 (m, 2H), 8.26-8.24 (m, 2H);

$^{13}$C NMR (125 MHz, CDCl$_3$) δ 161.3, 143.7, 126.1, 116.6, 99.8 (d, J=221 Hz).

Example 32

Preparation of N-(3-fluoromethoxyphenyl)acetamide (12j)

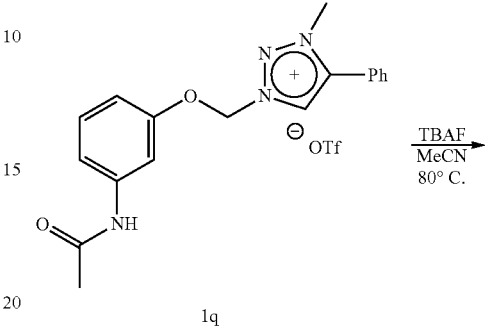

1q

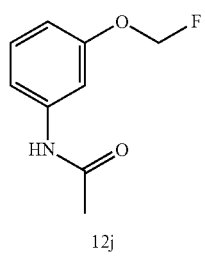

12j

N-(3-Fluoromethoxyphenyl)acetamide (12j, 70 mg, 76%) was obtained in the same manner as used in Example 21, except that 1-(4-acetylaminophenyl)oxymethyl-3-methyl-4-phenyl-1,2,3-triazolium trifluoromethanesulfonate (1q, 236 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 2.20 (s, 3H), 5.72 (d, J=54.5 Hz, 2H), 6.85 (d, J=7.0 Hz, 1H), 7.20 (d, J=7.5 Hz, 1H), 7.29-7.26 (m, 1H), 7.41 (s, 1H), 7.46 (br, 1H);

$^{13}$C NMR (125 MHz, CDCl$_3$) δ 168.7, 157.4, 139.5, 130.2, 115.0, 112.5, 108.7, 100.9 (d, J=218 Hz), 24.9

Example 33

Preparation of 3-O-fluoromethylestrone (12k)

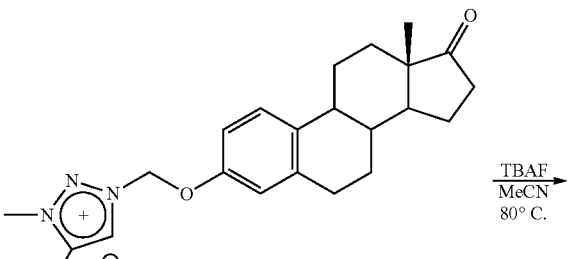

1r

-continued

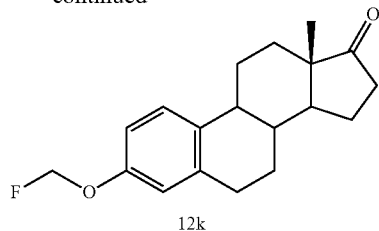

12k

3-O-Fluoromethylestrone (12k, 125 mg, 83%) was obtained in the same manner as used in Example 21, except that 1-(3-O-estronyl)methyl-3-methyl-4-phenyl-1,2,3-triazolium trifluoromethanesulfonate (1r, 296 mg, 0.5 mmol) was used, instead of 4-tert-butyl-3-methyl-1-[(2-naphthoxy)methyl]-1,2,3-triazolium trifluoromethanesulfonate (1a) of Example 21.

$^1$H NMR (500 MHz, CDCl$_3$) δ 0.89 (s, 3H), 1.66-1.39 (m, 7H), 2.16-1.93 (m, 5H), 2.25-2.20 (m, 1H), 2.40-2.36 (m, 1H), 2.48 (dd, J=19.0, 8.5 Hz, 1H), 2.89 (t, J=4.3 Hz, 2H), 5.66 (d, J=55.0 Hz, 2H), 6.81 (d, J=2.5 Hz, 1H), 6.86 (dd, J=8.5, 2.5 Hz, 1H), 7.22 (d, J=8.5 Hz, 4H);

$^{13}$C NMR (125 MHz, CDCl$_3$) δ 220.9, 155.1, 138.4, 135.2, 126.8, 117.0, 114.3, 101.1 (d, J=217 Hz), 50.6, 48.2, 44.2, 38.4, 36.1, 31.8, 29.8, 26.7, 21.8, 14.1

Example 34

Preparation of 3-O-[$^{18}$F]fluoromethylestron ([$^{18}$F]12k)

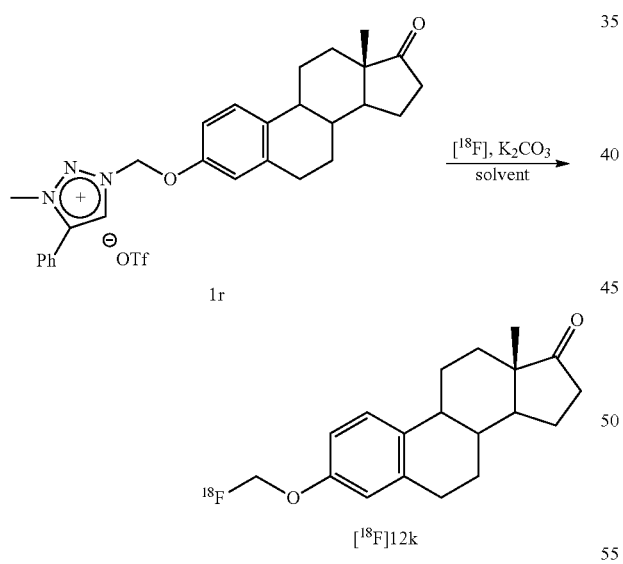

Distilled water (2.0 mL) and a 0.2 M sodium methanesulfonate aqueous solution (2.0 mL) were sequentially poured through a Chromafix® cartridge. The cartridge was washed once more with distilled water (2.0 mL). A [$^{18}$F] Fluoride [$^{18}$O]H$_2$O solution (1-10 mCi) produced from a cyclotron was slowly poured through the cartridge. The cartridge was washed with distilled water (2.0 mL). Methanol (2.0 mL) was poured through the cartridge holding [$^{18}$F]Fluoride so as to remove the water. A 0.1 M tetrabutylammonium methanesulfonate solution (0.5 mL) was poured through the cartridge so as to elute [$^{18}$F]Fluoride ions. The solution containing the eluted [$^{18}$F]Fluoride ions were heated to 100° C. while blowing nitrogen thereinto so as to remove the solvent. Subsequently, 1-(3-O-Estronyl)methyl-3-methyl-4-phenyl-1,2,3-triazolium trifluoromethanesulfonate (1r, 5 mg) was dissolved in acetonitrile or t-amyl alcohol and added thereto. Then, potassium carbonate (3 mg) was added thereto. The mixture was stirred for 20 minutes in the heating condition of 120° C. A yield of each of the reactions was measured by using Radio-TLC. The following Table 3 shows the measurement results.

TABLE 3

|  | acetonitrile | t-amyl alcohol |
|---|---|---|
| Radio-TLC (%) | 100 | 82 |

What is claimed is:
1. A precursor for the preparation of F-18 labeled radiopharmaceuticals represented by the following Chemical Formula 1:

[Chemical Formula 1]

wherein, in Chemical Formula 1,
$R_1$ is a part excluding a —X—CH$^2$—$^{18}$F part from an $^{18}$F-labeled radiotracer and represents a $C_1$-$C_{1000}$ hydrocarbon group in which a carbon in the main chain of the $C_1$-$C_{1000}$ hydrocarbon group may be non-replaced or replaced by an oxygen, a nitrogen, a sulfur, a phosphorus or combinations thereof and a hydrogen in the main chain may be non-replaced or replaced by a halogen,
X represents an oxygen, and
the leaving group is a salt consisting of (i) a tetravalent cation and (ii) an anion of Y, and the salt represents

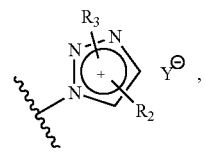

wherein one nitrogen within the ring of the tetravalent cation is substituted with $R_3$, and each carbon within the ring of the tetravalent cation may be independently non-substituted or substituted with $R_2$, respectively,
$R_2$ and $R_3$ are independently a $C_1$-$C_{20}$ hydrocarbon group in which a carbon in the main chain of the $C_1$-$C_{20}$ hydrocarbon group may be non-replaced or replaced by an oxygen, a nitrogen, a sulfur or combinations thereof, and a hydrogen in the main chain may be non-replaced or replaced by a halogen, and
Y is selected from the group consisting of trifluoromethanesulfonate (CF$_3$SO$_3^-$), paratoluenesulfonate, methanesulfonate and paranitrobenzenesulfonate.

2. The precursor for the preparation of F-18 labeled radiopharmaceuticals of claim 1,
wherein in Chemical Formula 1, $R_1$ represents a hydrocarbon $C_1$-$C_{200}$ group in which a carbon in the main chain of the $C_1$-$C_{200}$ hydrocarbon group may be non-replaced or replaced by an oxygen, a nitrogen, a sulfur, a phosphorus or combinations thereof and a hydrogen in the main chain may be non-replaced or replaced by a halogen.

3. The precursor for the preparation of F-18 labeled radiopharmaceuticals of claim 1, wherein in Chemical Formula 1, $R_1$ represents a $C_1$-$C_{100}$ hydrocarbon group in which a carbon in the main chain of the $C_1$-$C_{100}$ hydrocarbon group may be non-replaced or replaced by an oxygen, a nitrogen, a sulfur, a phosphorus or combinations thereof and a hydrogen in the main chain may be non-replaced or replaced by a halogen.

4. The precursor for the preparation of F-18 labeled radiopharmaceuticals of claim 1, wherein in Chemical Formula 1, $R_1$ is selected from the group consisting of

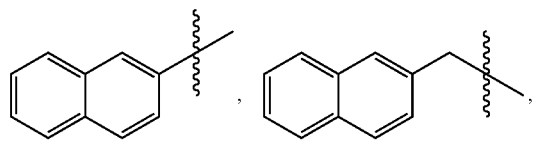

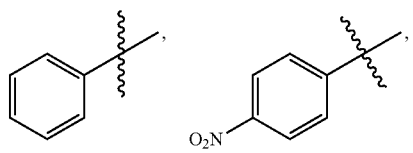

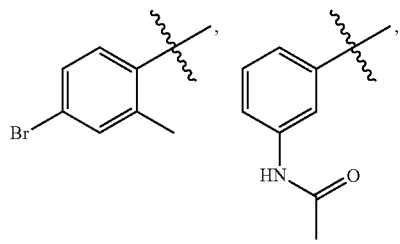

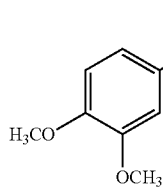

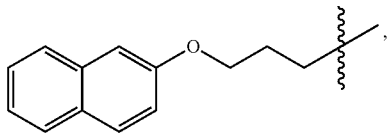

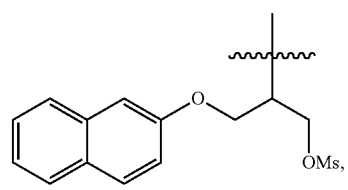

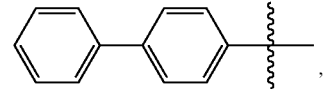

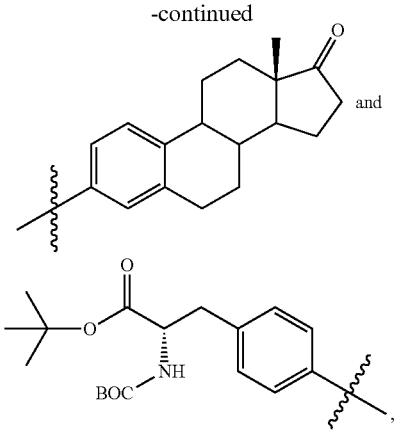

X represents an oxygen, and
$R_2$ and $R_3$ are independently selected from the group consisting of a straight or branched chain of $C_{1-4}$ alkyl group, phenyl,

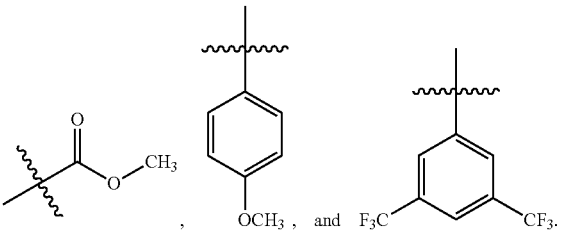

5. The precursor for the preparation of F-18 labeled radiopharmaceuticals of claim 1, wherein the precursor represented by Chemical Formula 1 is selected from the group consisting of 4-tert-butyl-3-methyl-1-[(2-naphthoxy)methyl]-1,2,3-triazolium trifluoromethanesulfonate;

4-methoxycarbonyl-3-methyl-1-[(2-naphthoxy)methyl]-1,2,3-triazolium trifluoromethanesulfonate;

4-[3,5-di(trifluoromethyl)phenyl]-3-methyl-1-[(2-naphthoxy)methyl]-1,2,3-triazolium trifluoromethanesulfonate;

4-(4-methoxyphenyl)-3-methyl-1-[(2-naphthoxy)methyl]-1,2,3-triazolium trifluoromethanesulfonate;

3-methyl-1-[(2-naphthoxy)methyl]-4-phenyl-1,2,3-triazolium trifluoromethanesulfonate;

3-methyl-1-[3-(2-naphthoxy)-n-propyl]oxymethyl-4-phenyl-1,2,3-triazolium trifluoromethanesulfonate;

1-[1-methylsulfonyloxy-3-(2-naphthyl)-2-oxypropyl]oxymethyl-3-methyl-4-phenyl-1,2,3-triazolium trifluoromethanesulfonate;

3-methyl-(2-naphthyl)methyloxymethyl-4-phenyl-1,2,3-triazolium trifluoromethanesulfonate;

(s)-1-[4-[2-BOC-amino-2-(t-butoxycarbonyl)ethyl]phenyloxymethyl]-4-phenyl-1,2,3-triazolium trifluoromethanesulfonate;

1-(4-biphenyl)oxymethyl-3-methyl-4-phenyl-1,2,3-triazolium trifluoromethanesulfonate;

1-(4-bromo-2-methylphenyl)oxymethyl-3-methyl-4-phenyl-1,2,3-triazolium trifluoromethanesulfonate;

1-(3,4-dimethoxyphenyl)oxymethyl-3-methyl-4-phenyl-1,2,3-triazolium trifluoromethanesulfonate;

3-methyl-1-(4-nitrophenyl)oxymethyl-4-phenyl-1,2,3-triazolium trifluoromethanesulfonate;

1-(4-acetylaminophenyl)oxymethyl-3-methyl-4-phenyl-1,2,3-triazolium trifluoromethanesulfonate; and,
1-(3-O-estronyl)methyl-3-methyl-4-phenyl-1,2,3-triazolium trifluoromethanesulfonate.

* * * * *